(12) United States Patent
Giresi et al.

(10) Patent No.: US 11,597,974 B2
(45) Date of Patent: *Mar. 7, 2023

(54) TRANSPOSITION OF NATIVE CHROMATIN FOR PERSONAL EPIGENOMICS

(71) Applicant: The Board of Trustees of the Leland Stanford Junior University, Stanford, CA (US)

(72) Inventors: Paul Giresi, Palo Alto, CA (US); Jason D. Buenrostro, Redwood City, CA (US); Howard Y. Chang, Stanford, CA (US); William J. Greenleaf, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/833,686

(22) Filed: Jun. 6, 2022

(65) Prior Publication Data

US 2022/0325342 A1 Oct. 13, 2022

Related U.S. Application Data

(63) Continuation of application No. 17/114,278, filed on Dec. 7, 2020, which is a continuation of application No. 16/918,924, filed on Jul. 1, 2020, now Pat. No. 10,889,859, which is a continuation of application No. 16/418,796, filed on May 21, 2019, now Pat. No. 10,738,357, which is a continuation of application No. 16/160,719, filed on Oct. 15, 2018, now Pat. No. 10,337,062, which is a continuation of application No. 16/043,874, filed on Jul. 24, 2018, now Pat. No. 10,150,995, which is a continuation of application No. 14/784,250, filed as application No. PCT/US2014/038825 on May 20, 2014, now Pat. No. 10,059,989.

(60) Provisional application No. 61/826,728, filed on May 23, 2013.

(51) Int. Cl.
  *C12Q 1/6874* (2018.01)
  *C12Q 1/6869* (2018.01)
  *C12Q 1/6806* (2018.01)
  *G16B 30/00* (2019.01)
  *G16H 50/20* (2018.01)
  *G16B 20/00* (2019.01)

(52) U.S. Cl.
  CPC ......... *C12Q 1/6874* (2013.01); *C12Q 1/6806* (2013.01); *C12Q 1/6869* (2013.01); *G16B 30/00* (2019.02); *C12Q 2521/301* (2013.01); *C12Q 2537/164* (2013.01); *G16B 20/00* (2019.02); *G16H 50/20* (2018.01)

(58) Field of Classification Search
  CPC ............... C12Q 1/6874; C12Q 1/6806; C12Q 1/6869; C12Q 2521/301; C12Q 2537/164; G16B 30/00; G16B 20/00; G16H 50/20
  See application file for complete search history.

(56) References Cited

U.S. PATENT DOCUMENTS

| | | |
|---|---|---|
| 5,137,829 A | 8/1992 | Nag et al. |
| 5,965,443 A | 10/1999 | Reznikoff et al. |
| 6,159,717 A | 12/2000 | Savakis et al. |
| 6,207,384 B1 | 3/2001 | Mekalanos et al. |
| 6,258,571 B1 | 7/2001 | Chumakov et al. |
| 6,291,243 B1 | 9/2001 | Fogarty et al. |
| 6,294,385 B1 | 9/2001 | Goryshin et al. |
| 6,593,113 B1 | 7/2003 | Tenkanen et al. |
| 6,613,752 B2 | 9/2003 | Kay et al. |
| 7,138,267 B1 | 11/2006 | Jendrisak et al. |
| 7,608,434 B2 | 10/2009 | Reznikoff et al. |
| 7,608,451 B2 | 10/2009 | Cooper et al. |
| 7,745,218 B2 | 6/2010 | Kim et al. |
| 8,124,404 B2 | 2/2012 | Alphey |
| 8,420,386 B2 | 4/2013 | Ivics et al. |
| 8,598,328 B2 | 12/2013 | Koga et al. |
| 8,829,171 B2 | 9/2014 | Steemers et al. |
| 8,927,218 B2 | 1/2015 | Forsyth |
| 9,005,935 B2 | 4/2015 | Belyaev |
| 9,074,251 B2 | 7/2015 | Steemers et al. |
| 9,080,211 B2 | 7/2015 | Grunenwald et al. |

(Continued)

FOREIGN PATENT DOCUMENTS

| | | |
|---|---|---|
| CN | 102292455 | 12/2011 |
| WO | WO 2007/093819 | 8/2007 |

(Continued)

OTHER PUBLICATIONS

Park et al., Nature 10, 669-680, (Year: 2009).*
Gertz et al., Genome Research, 22(1): 134-141, Jan. 2012.*
Biery et al., "A simple in vitro Tn7-based transposition system with low target site selectivity for genome and gene analysis", Nucleic Acids Research, 2000, 28(5): 1067-1077.
Brouilette et al., "A Simple and Novel Method for RNA-seq Library Preparation of Single Cell cDNA Analysis by Hyperactive Tn5 Transposase", Developmental Dynamics, 2012, 241:1584-1590.

(Continued)

*Primary Examiner* — Cynthia B Wilder
(74) *Attorney, Agent, or Firm* — Casimir Jones, S.C.; Tanya A. Arenson

(57) ABSTRACT

Provided herein is a method for analyzing polynucleotides such as genomic DNA. In certain embodiments, the method comprises: (a) treating chromatin isolated from a population of cells with an insertional enzyme complex to produce tagged fragments of genomic DNA; (b) sequencing a portion of the tagged fragments to produce a plurality of sequence reads; and (c) making an epigenetic map of a region of the genome of the cells by mapping information obtained from the sequence reads to the region. A kit for performing the method is also provided.

30 Claims, 24 Drawing Sheets

Specification includes a Sequence Listing.

(56) References Cited

U.S. PATENT DOCUMENTS

| | | | |
|---|---|---|---|
| 9,150,916 | B2 | 10/2015 | Christen et al. |
| 9,175,295 | B2 | 11/2015 | Kaminaka et al. |
| 9,238,671 | B2 | 1/2016 | Goryshin et al. |
| 9,328,382 | B2 | 5/2016 | Drmanac et al. |
| 9,574,226 | B2 | 2/2017 | Gormley et al. |
| 10,059,989 | B2 * | 8/2018 | Giresi ............... C12Q 1/6874 |
| 10,689,643 | B2 | 6/2020 | Jelinek et al. |
| 10,889,859 | B2 * | 1/2021 | Giresi ............... G16H 50/20 |
| 11,306,307 | B2 | 4/2022 | Jelinek et al. |
| 2003/0032141 | A1 | 2/2003 | Nguyen |
| 2004/0101880 | A1 | 5/2004 | Rozwadowski et al. |
| 2010/0120098 | A1 | 5/2010 | Grunenwald et al. |
| 2011/0306042 | A1 | 12/2011 | Jouvenot |
| 2012/0297493 | A1 | 11/2012 | Cooper et al. |
| 2013/0079251 | A1 | 3/2013 | Boles |
| 2013/0203605 | A1 | 8/2013 | Shendure et al. |
| 2014/0274740 | A1 | 9/2014 | Srinivasan et al. |
| 2015/0111788 | A1 | 4/2015 | Fernandez et al. |
| 2015/0267191 | A1 | 9/2015 | Steelman et al. |
| 2015/0337298 | A1 | 11/2015 | Xi et al. |
| 2015/0368638 | A1 | 12/2015 | Steemers et al. |
| 2015/0376608 | A1 | 12/2015 | Kaper et al. |
| 2016/0060691 | A1 | 3/2016 | Giresi et al. |
| 2016/0115474 | A1 * | 4/2016 | Jelinek ............... C12Q 1/6804 506/28 |
| 2016/0122753 | A1 | 5/2016 | Mikkelsen et al. |
| 2016/0160235 | A1 | 6/2016 | Solodushko et al. |
| 2016/0177359 | A1 | 6/2016 | Ukanis et al. |
| 2016/0208323 | A1 | 7/2016 | Bernstein et al. |
| 2016/0376663 | A1 | 12/2016 | Brown |

FOREIGN PATENT DOCUMENTS

| | | |
|---|---|---|
| WO | WO 2009/147386 | 12/2009 |
| WO | WO 2010/048605 | 4/2010 |
| WO | WO2012106546 | 8/2012 |
| WO | WO 2013/181265 A1 | 12/2013 |
| WO | WO 2014/108810 | 7/2014 |
| WO | WO 2014/190214 | 11/2014 |
| WO | WO 2016/191618 | 12/2016 |
| WO | WO 2016/207647 | 12/2016 |
| WO | WO 2016/207653 | 12/2016 |
| WO | WO 2016/207661 | 12/2016 |
| WO | WO 2017/015075 | 1/2017 |
| WO | WO 2017/025594 | 2/2017 |

OTHER PUBLICATIONS

Gangadharan et al., "DNA transposon Hermes inserts into DNA in nucleosome-free regions in vivo", PNAS, 2010, 107(51): 21966-21972.

Goryshin et al., "Tn5 in Vitro Transposition", The Journal of Biological Chemistry, 1998, 273(13): 7367-7374.

Haapa et al., "An Efficient DNA Sequencing Strategy Based on the Bacteriophage Mu in Vitro DNA Transposition Reaction", Genome Research, 1999, 9(3):308-315.

Hickman et al., "Molecular architecture of a eukaryotic DNA transposase", Nature Structural & Molecular Biology, 2005, 12(8): 715-721.

O'Brochta et al., "Hemes, a Functional Non-Drosophilid Insect Gene Vector From Musca domestica", Genetics, 1996, 142: 907-914.

Perez et al., "Purification, crystallization and preliminary crystallographic analysis of the Hermes transposase", Acta Crystallographica, 2005, F61, 587-590.

Zhou et al., "Transposition of hAT elements links transposable elements and V(D)J recombination", Nature, 2004, 432: 995-1001.

NCBI, GenBank accession No. AAB60236.1 (Oct. 19, 1995).

NCBI, GenBank accession No. L34807.1 (May 24, 2005).

Adey, et al., "Ultra-low-input, tagmentation-based whole-genome bisulfite sequencing", Genome Research, 2012, 22(6): 1139-1143.

Ason et al., "DNA Sequence Bias During Tn5 Transposition", J. Mol. Biol., 2004, 335: 1213-1255.

Bjornsson et al., Intra-individiual change over time in DNA methylation with familial clustering, JAMA, Jun. 25, 2008, vol. 299 No. 24, pp. 2877-2883.

Boyle, et al., "High-resolution genome-wide in vivo footprinting of diverse transcription factors in human cells", Genome Res. Mar. 2011;21(3):456-64.

Buenrostro, et al., "Tranposition of native chromatin for fast and sensitive epigenomic profiling of open chromatin, DNA-binding proteins and nucleosome position", Nature Methods, 2013, 10(12): 1213-1218.

Gangadharan et al., DNA transposon Hermes insert into DNA in nucleosome-free regions in vivo, Proc nat Ad Sci, Dec. 21, 2010, vol. 107, No. 51, pp. 1966-1972.

Green et al., "Insertion site preference of Mu, Tn5, and Tn7 transposons", Mobile DNA, 2012, 3:3, 6 pages.

Parks et al., "ChIP-Seq: advantages and challenges of a maturing technology", Nature, vol. 10, pp. 669-680, Oct. 2009.

Haring et al., "Chromatin immunoprecipitation: optimization, quantitative analysis and data normalization", Plant Methods, 3 (11): 1-25 (Year: 2007).

Simon, et al., "Using formaldehyde-assisted isolation of regulatory elements (FAIRE) to isolate active regulatory DNA", Nature Protocols, 2012, 7(2): 256-267.

Song, et al., "DNase-seq: A High-Resolution Technique for Mapping Active Gene Regulatory Elements across the Genome from Mammalian Cells", Cold Spring Harbor Laboratory Press, 2010, 2010(2), doi:10.1101/pdb.prot5384.

Zentner et al., "Surveying the epigenomic landscape, one base at a time", Genome Biology, 2012, 13:250, 8 pages.

Epicentre., "EZ-Tn5® Custom Transposome Construction Kits", www.epicentre.com, pp. 1-17, 2012.

Ahern, "Tools & Technology, Biochemical, Reagent Kits Offer Scientists Good Return on Investment", The Scientist, 1995, vol. 20, pp. 20 and 22.

Audit et al., "Open chromatin encoded in DNA sequence is the signature of 'master' replication origins in human cells", Nucleic Acids Research, 2009, 37(18): 6064-6075.

Adey et al., "Rapid, low-input, low-bias construction of shotgun fragment libraries by high-density in vitro transposition", Genome Biology, 2010, 11: R119, 17 pages.

Gangadharan et al., Supporting Information for "DNA transposon Hermes inserts into DNA in nucleosome-free regions in vivo", PNAS, 2010, 107 (51) 21966-21972.

Guimond et al., "Patterns of Hermes transposition in Drosophila melanogaster", Molecular Genetics and Genomics, 2003, 268: 779-790.

* cited by examiner

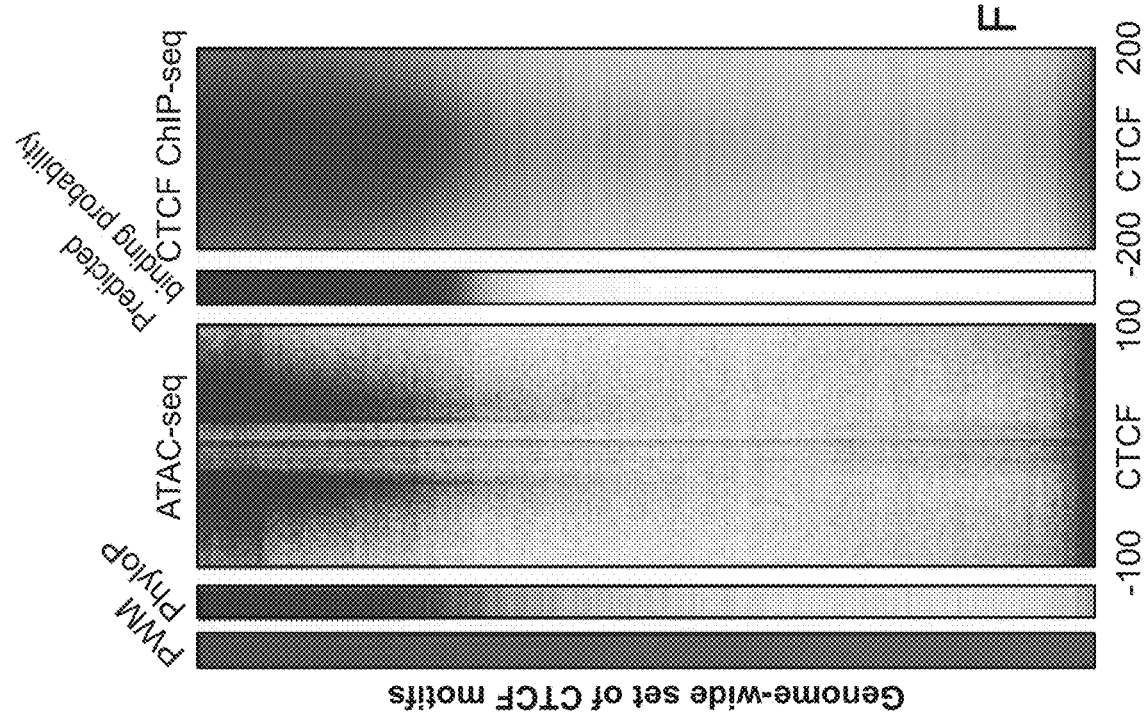
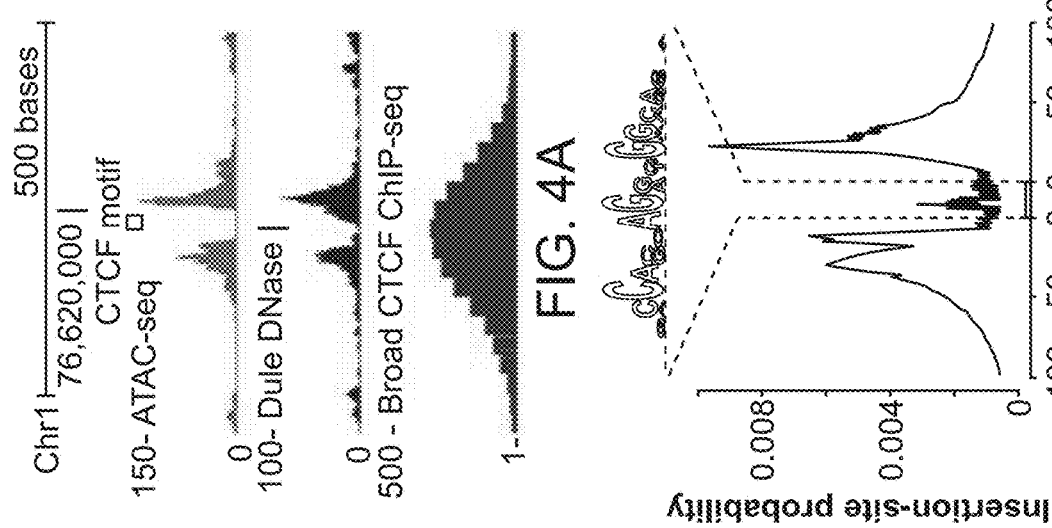
FIG. 4A
FIG. 4B
FIG. 4C

SEQUENCE LISTING

<160> NUMBER OF SEQ ID NOS: 25

<210> SEQ ID NO 1
<211> LENGTH: 50
<212> TYPE: DNA
<213> ORGANISM: Artificial Sequence
<220> FEATURE:
<223> OTHER INFORMATION: synthetic polynucleotide

<400> SEQUENCE: 1
aatgatacgg cgaccaccga gatctacact cgtcggcagc gtcagatgtg    50

<210> SEQ ID NO 2
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 2
caagcagaag acggcatacg agattcgcct tagtctcgtg gctcggaga tgt    53

<210> SEQ ID NO 3
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 3
caagcagaag acggcatacg agatctagta cggtctcgtg gctcggaga tgt    53

<210> SEQ ID NO 4
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 4
caagcagaag acggcatacg agatttctgc ctgtctcgtg gctcggaga tgt    53

<210> SEQ ID NO 5
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 5
caagcagaag acggcatacg agatgctcag gagtctcgtg gctcggaga tgt    53

<210> SEQ ID NO 6
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 6
caagcagaag acggcatacg agataggagt ccgtctcgtg gctcggaga tgt    53

<210> SEQ ID NO 7
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 7
caagcagaag acggcatacg agatcatgcc tagtctcgtg ggctcggaga tgt         53

<210> SEQ ID NO 8
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 8
caagcagaag acggcatacg agatgtagag aggtctcgtg ggctcggaga tgt         53

<210> SEQ ID NO 9
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 9
caagcagaag acggcatacg agatcctctc tggtctcgtg ggctcggaga tgt         53

<210> SEQ ID NO 10
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 10
caagcagaag acggcatacg agatagcgta gcgtctcgtg ggctcggaga tgt         53

<210> SEQ ID NO 11
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 11
caagcagaag acggcatacg agatcagcct cggtctcgtg ggctcggaga tgt         53

<210> SEQ ID NO 12
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 12
caagcagaag acggcatacg agattgcctc ttgtctcgtg ggctcggaga tgt         53

<210> SEQ ID NO 13
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 13
caagcagaag acggcatacg agattcctct acgtctcgtg ggctcggaga tgt         53

<210> SEQ ID NO 14
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 14
caagcagaag acggcatacg agatatcacg acgtctcgtg ggctcggaga tgt    53

<210> SEQ ID NO 15
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 15
caagcagaag acggcatacg agatacagtg gtgtctcgtg ggctcggaga tgt    53

<210> SEQ ID NO 16
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 16
caagcagaag acggcatacg agatcagatc cagtctcgtg ggctcggaga tgt    53

<210> SEQ ID NO 17
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 17
caagcagaag acggcatacg agatacaaac gggtctcgtg ggctcggaga tgt    53

<210> SEQ ID NO 18
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 18
caagcagaag acggcatacg agatacccag cagtctcgtg ggctcggaga tgt    53

<210> SEQ ID NO 19
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 19
caagcagaag acggcatacg agataacccc tcgtctcgtg ggctcggaga tgt    53

<210> SEQ ID NO 20
<211> LENGTH: 53
<212> TYPE: DNA
<213> ORGANISM: Artificial sequence
<220> FEATURE:
<223> OTHER INFORMATION: synthetic polynucleotide

```
<400> SEQUENCE: 20
caagcagaag acggcatacg agatcccaac ctgtctcgtg ggctcggaga tgt          53

<210> SEQ ID NO 21
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 21
caagcagaag acggcatacg agatcaccac acgtctcgtg ggctcggaga tgt          53

<210> SEQ ID NO 22
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 22
caagcagaag acggcatacg agatgaaacc cagtctcgtg ggctcggaga tgt          53

<210> SEQ ID NO 23
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 23
caagcagaag acggcatacg agattgtgac cagtctcgtg ggctcggaga tgt          53

<210> SEQ ID NO 24
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 24
caagcagaag acggcatacg agatagggtc aagtctcgtg ggctcggaga tgt          53

<210> SEQ ID NO 25
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 25
caagcagaag acggcatacg agataggagt gggtctcgtg ggctcggaga tgt          53
```

TRANSPOSITION OF NATIVE CHROMATIN FOR PERSONAL EPIGENOMICS

CROSS-REFERENCING

This application is a continuation of U.S. patent application Ser. No. 17/114,278, filed on Dec. 7, 2020, which is a continuation of U.S. patent application Ser. No. 16/918,924, filed on Jul. 1, 2020, now issued as U.S. Pat. No. 10,889,859, which is a continuation of U.S. patent application Ser. No. 16/418,796, filed on May 21, 2019, now issued as U.S. Pat. No. 10,738,357, which is a continuation of U.S. patent application Ser. No. 16/160,719, filed on Oct. 15, 2018, now issued as U.S. Pat. No. 10,337,062, which is a continuation of U.S. patent application Ser. No. 16/043,874, filed on Jul. 24, 2018, now issued as U.S. Pat. No. 10,150,995, which is a continuation of U.S. patent application Ser. No. 14/784,250, filed on Oct. 13, 2015, now issued as U.S. Pat. No. 10,059,989, which application is a § 371 national phase filing of International Application No. PCT/US2014/038825, filed on May 20, 2014, which application claims the benefit of U.S. Provisional application Ser. No. 61/826,728, filed on May 23, 2013, which applications are incorporated by reference herein in their entirety.

GOVERNMENT SUPPORT

This invention was made with Government support under contracts AI057229, HG000044, and NS073015 awarded by the National Institutes of Health. The Government has certain rights in the invention.

BACKGROUND

Eukaryotic genomes are hierarchically packaged into chromatin, and the nature of this packaging plays a central role in gene regulation. Major insights into the epigenetic information encoded within the nucleoprotein structure of chromatin have come from high-throughput, genome-wide methods for separately assaying the chromatin accessibility ("open chromatin"), nucleosome positioning, and transcription factor (TF) occupancy. While published protocols exist, those methods require millions of cells as starting material, complex and time-consuming sample preparations, and cannot simultaneously probe the interplay of nucleosome positioning, chromatin accessibility, and TF binding. These limitations are problematic in three major ways: First, current methods can average over and "drown out" heterogeneity in cellular populations. Second, cells must often be grown ex vivo to obtain sufficient biomaterials, perturbing the in vivo context and modulating the epigenetic state in unknown ways. Third, input requirements often prevent application of these assays to well-defined clinical samples, precluding generation of "personal epigenomes" in diagnostic timescales. Provided herein are methods for analyzing polynucleotides, including their accessibility and their structure, that can overcome these limitation(s). Also provided are single-cell methods that can provide higher sensitivity and further information on chromatin accessibility, including cell-to-cell variability, to potentially enable its use as a biomarker.

SUMMARY

Provided herein is a method for analyzing polynucleotides such as genomic DNA. In certain embodiments, the method comprises: (a) treating chromatin isolated from a population of cells with a transposase and molecular tags to produce tagged fragments of polynucleotides; (b) sequencing a portion of the tagged fragments to produce a plurality of sequence reads; and (c) making an epigenetic map of a region of the genome of the cells by mapping information obtained from the sequence reads to the region.

In some cases, the information is obtained using the nucleotide sequences at the beginning and, optionally, the end of a sequence read. In some cases, the information mapped in (c) is selected from one or more of: (i) cleavage sites for the transposase; (ii) the sizes of the fragments produced in step (a); (iii) sequence read length; (iii) the positions of sequence reads of a defined range in length; and (iv) sequence read abundance. In some instances, the fragments of a defined size range are nucleosome-free fragments.

In some instances, the epigenetic map shows one or more of: (i) a profile of chromatin accessibility along the region; (ii) DNA binding protein occupancy for a binding site in the region; (iii) nucleosome-free DNA in the region; (iv) positioning of nucleosomes along the region; and/or (v) chromatin states. In some cases, the method can further comprise measuring global occupancy of a binding site for the DNA binding protein. The DNA binding protein can, for example, be a transcription factor.

In some cases, the population of cells can be composed of about 500 to 100,000 cells. The cells can be isolated from an individual, such as from the blood of the individual. In some examples, the cells can be of the same cell type. In some examples, the cells can be FACS-selected cells.

In some instances, the treating step (a) can comprise: isolating nuclei from the population of cells; and combining the isolated nuclei with the insertional enzyme complex, wherein the combining results in both lysis of the nuclei to release the chromatin and production of the tagged fragments of genomic DNA. In some examples, the transposase can be derived from Tn5 transposase. In other examples, the transposase can be derived from MuA transposase. In further examples, the transposase can be derived from Vibhar transposase (e.g. from *Vibrio harveyi*).

The present disclosure also provides a method for comparing two samples comprising: (a) analyzing a first population of cells to produce a first epigenetic map; and (b) analyzing a second population of cells to produce a second epigenetic map; and (c) comparing the first epigenetic map to the second epigenetic map. For example, the first population of cells and the second population of cells can be collected from the same individual at different times. Alternatively, the first population of cells and the second population of cells can be different populations of cells collected from different individuals.

The present disclosure further provides a diagnostic method, comprising: analyzing chromatin from a patient to produce an epigenetic map; and providing a diagnosis or prognosis based on the epigenetic map.

The present disclosure provides a method for determining accessibility of a polynucleotide at a site, wherein the polynucleotide is from a cell sample, comprising: (a) inserting a plurality of molecular tags with an insertional enzyme into the polynucleotide; and (b) using the molecular tags to determine accessibility at the site. The method can further comprise using the determined accessibility to identify one or more proteins that are bound to the polynucleotide at the site. In some cases, at least one of the proteins is a transcription factor. The method can also comprise using the molecular tags to generate an accessibility map of the polynucleotide.

The present disclosure also provides a method for analyzing the three-dimensional structure of a polynucleotide from a cell sample, comprising: (a) inserting a plurality of molecular tags with an insertional enzyme into the polynucleotide; and (b) using the molecular tags to analyze the three-dimensional structure of the polynucleotide. In some cases, the insertional enzyme can comprise two or more enzymatic moieties wherein each of the enzymatic moieties inserts a common sequence into the polynucleotide. The enzymatic moieties can be linked together. The common sequence can comprise a common barcode. The enzymatic moieties can comprise transposases. The polynucleotide can fragmented into a plurality of fragments during step (a), wherein the fragments comprising the common barcode are determined to be in proximity in the three-dimensional structure of the polynucleotide.

The polynucleotide can be fragmented into a plurality of fragments during the insertion. The method can further comprise amplifying the fragments. The accessibility can be determined by sequencing the fragments and thereby generating a plurality of sequencing reads. The fragments can, for example, be sequenced by a high-throughput sequencing technique. The method can further comprise normalizing the sequencing reads based on the sequence insertion preference of the insertional enzyme. The length of the sequenced reads can also be used to determine a chromatin state annotation.

The cell sample can be permeabilized to allow access for the insertional enzyme. In some cases, the nuclei in the cell sample can be minimally perturbed during the permeabilization. The cell sample can be permeabilized using a permeabilization agent including, but not limited to, NP40, digitonin, tween, streptolysin, and/or cationic lipids. The cell sample can also be permeabilized using hypotonic shock and/or ultrasonication.

The method can further comprise analyzing a disease state in a subject based on the accessibility of the specific site, wherein the cell sample is obtained from the subject. The cell sample and/or the polynucleotides can also be divided into a plurality of portions, which may be optionally divided based on the molecular tags. The method can further comprise analyzing a phenotype of the cell sample. In some cases, the phenotype can be correlated to the accessibility of the site.

The insertion can be facilitated by addition of one or more divalent cations. In some cases, the one or more divalent cations can comprise magnesium. In some cases, the one or more divalent cations can comprise manganese.

The cell sample can be obtained from a primary source. The cell sample can consist of less than about 500,000 cells, or even a single cell. The polynucleotide can be bound to a plurality of association molecules. The association molecules can comprise proteins, such as histones. The insertional enzyme can be a transposase. In some cases, the transposase can be derived from a Tn5 transposase. In other cases, the transposase can be derived from a MuA transposase. In further cases, the transposase can be derived from a Vibhar transposase (e.g. from *Vibrio harveyi*). In some cases, the molecular tags can comprise sequencing adaptors, which may further comprise a barcode label. The barcode label can comprise a unique sequence. In other cases, the molecular tags can comprise fluorescence tags. The insertional enzyme can further comprise an affinity tag, which may optionally be an antibody that binds to a transcription factor, a modified nucleosome, and/or a modified nucleic acid. The modified nucleic acid can, for example be a methylated or hydroxymethylated DNA. The affinity tag can also be a single-stranded nucleic acid, which may optionally bind to a target nucleic acid. The insertional enzyme can further comprise a nuclear localization signal.

The present disclosure also provides compositions. The composition can comprise a polynucleotide, an insertional enzyme and an insert element, wherein: the insert element comprises a nucleic acid comprising a predetermined sequence; and the insertional enzyme further comprises an affinity tag. The composition can also comprise a polynucleotide, an insertional enzyme and an insert element, wherein: the insertional enzyme comprises two or more enzymatic moieties; and the enzymatic moieties are linked together. The affinity tag can be an antibody, which may optionally be bound to a transcription factor, a modified nucleosome, and/or a modified nucleic acid. The modified nucleic acid can be, for example, a methylated or hydroxymethylated DNA. The affinity tag can also be a single-stranded nucleic acid, which may be optionally bound to a target nucleic acid. The insert element can be bound to the insertional enzyme and the insertional enzyme is bound to the polynucleotide. The polynucleotide can be further bound to a plurality of association molecules. The association molecules can comprise proteins such as, for example, histones.

The present disclosure further provides kits. The kit can comprise: (a) reagents for isolating nuclei from a population of cells; (b) an insertional enzyme complex, and (c) transposase reaction buffer. In some cases, the components of the kit can be configured such that, combining the reaction buffer, transposon tags and adaptors with nuclei in vitro results in both lysis of the nuclei to release chromatin and production of tagged fragments of genomic DNA. The kit can also comprise: a cell lysis buffer; an insertional enzyme comprising an affinity tag; and an insert element comprising a nucleic acid, wherein the nucleic acid comprises a predetermined sequence. The kit can further comprise: a cell lysis buffer; an insertional enzyme comprising two or more enzymatic moieties, wherein the enzymatic moieties are linked together; and (c) an insert element. The affinity tag can be an antibody, which can optionally bind to a transcription factor, a modified nucleosome, and/or a modified nucleic acid. The modified nucleic acid can be, for example, a methylated or hydroxymethylated DNA. The affinity can also be a single-stranded nucleic acid, which may be optionally bound to a target nucleic acid.

These and other features of the present teachings are set forth herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The skilled artisan will understand that the drawings, described below, are for illustration purposes only. The drawings are not intended to limit the scope of the present teachings in any way.

FIGS. 4A-4C: ATAC-seq assays genome-wide factor occupancy. (a) CTCF footprints observed in ATAC-seq and DNase-seq data, at a specific locus on chr1. (b) Aggregate ATAC-seq footprint for CTCF (motif shown) generated over binding sites within the genome (c) CTCF predicted binding probability inferred from ATAC-seq data, position weight matrix (PWM) scores for the CTCF motif, and evolutionary conservation (PhyloP). Right-most column is the CTCF ChIP-seq data (ENCODE) for this GM12878 cell line, demonstrating high concordance with predicted binding probability.

DEFINITIONS

Figure 1A:
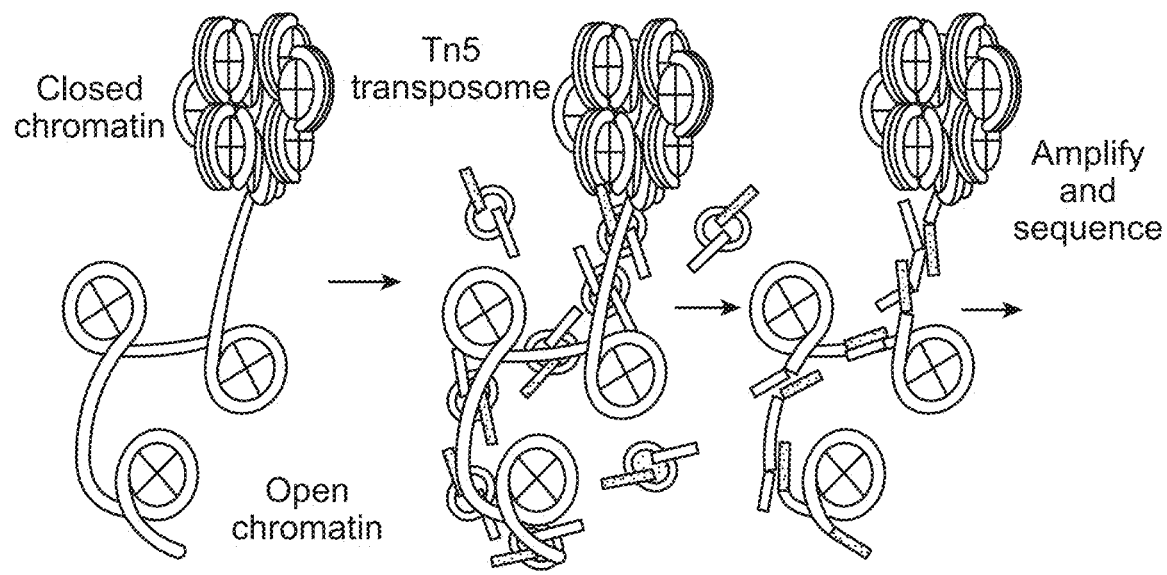
FIGS. 1A-1C: ATAC-seq is a sensitive, accurate probe of open chromatin state. (a) ATAC-seq reaction schematic. Transposase (green), loaded with sequencing adapters (red and blue), inserts only in regions of open chromatin (nucleosomes in grey) and generates sequencing library fragments that can be PCR amplified. (b) Approximate reported input material and sample preparation time requirements for genome-wide methods of open chromatin analysis. (c) A comparison of ATAC-seq to other open chromatin assays at a locus in GM12878 lymphoblastoid cells displaying high concordance. Lower ATAC-seq track was generated from 500 FACS-sorted cells.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "nucleic acid sample," as used herein, denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. A DNA target may originate from any source such as genomic DNA, or an artificial DNA construct. Any sample containing nucleic acid, e.g., genomic DNA from tissue culture cells or a sample of tissue, may be employed herein.

The term "mixture," as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide"

includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a region of nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strand region in a hybridization reaction. The hybridization reaction can be made to be highly specific by adjustment of the hybridization conditions (often referred to as hybridization stringency) under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotide region that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acids, which are produced from the amplifying process as defined herein.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "ligating," as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

If two nucleic acids are "complementary," they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing" refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences.

The term "barcode sequence" or "molecular barcode," as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide. Barcode sequences may vary widely in size and composition; the following references provide guidance for selecting sets of barcode sequences appropriate for particular embodiments: Brenner, U.S. Pat. No. 5,635, 400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "in vitro" refers to a reaction that occurs in a vessel with isolated components, not in cells.

The term "distributed" in the context of cleavage sites that are distributed along the length of a target nucleic acid molecule, refers to insertions that are spaced from another along the length of the target nucleic acid molecule. There is no requirement that all of the insertions are spaced by the same amount. Rather, spacing between insertions may be random, semi-random, or not random.

The term "chromatin," as used herein, refers to a complex of molecules including proteins and polynucleotides (e.g. DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

The term "treating," as used herein, refers to combining under conditions (e.g., a suitable temperature, time and conditions) that result in a reaction, e.g., cleavage.

The term "chromatin isolated from a population of cells," as used herein, refers to a source of chromatin that is caused to be made available. Isolated nuclei (which can be lysed to produce chromatin) as well as isolated chromatin (i.e., the product of lysed nuclei) are both considered types of chromatin isolated from a population of cells.

The term "transcription factor", as used herein, refers to any polypeptide that may act by itself or in combination with at least one other polypeptide to regulate gene expression levels. The term includes, but is not limited to, polypeptides that directly bind DNA sequences. Transcription factors can either increases or suppress expression levels. Examples of transcription factors include, but are not limited to Myc/Max, AP-1 (Jun, Fos, ATF), CREB, SMAD, HIF, ETS, ERG, ELK, STAT, estrogen receptor (ER), androgen receptor (AR), glucocorticoid receptor (GR), progesterone receptor (PR), NFκB, p53, OCT, SOX and PAX. The transcription factor may be a transcription factor identified by sequence analysis or a naturally-occurring reading frame sequence that has not been previously characterized as a transcription factor. The polypeptide may also be an artificially generated or chemically or enzymatically modified polypeptide.

The term "insertional enzyme complex," as used herein, refers to a complex comprising an insertional enzyme and two adaptor molecules (the "transposon tags") that are combined with polynucleotides to fragment and add adaptors to the polynucleotides. Such a system is described in a variety of publications, including Caruccio (Methods Mol. Biol. 2011 733: 241-55) and US20100120098, which are incorporated by reference herein.

The term "tagged fragments," as used herein, refers to polynucleotide fragments that are attached to tags.

The term "region," as used herein, refers to a contiguous length of nucleotides in a genome of an organism. A chromosomal region may be in the range of 1 bp to the length of an entire chromosome. In some instances, a region may have a length of at least 200 bp, at least 500 bp, at least 1 kb, at least 10 kb or at least 100 kb or more (e.g., up to 1 Mb or 10 Mb or more). The genome may be from any eukaryotic organism, e.g., an animal or plant genome such as the genome of a human, monkey, rat, fish or insect.

The term "epigenetic map," as used herein, refers to any representation of epigenetic features, e.g., sites of nucleosomes, nucleosome-free regions, binding sites for transcription factors, etc. A map can be physically displayed, e.g., on a computer monitor. Exemplary epigenetic maps are shown in FIGS. 1C, 3A, 4A, 4B, 5B and 5C.

The term "mapping information," as used herein, refers to assembling experimentally-obtained information about an area to a physical map of the area.

The term "sequence read abundance," as used herein, refers to the number of times a particular sequence or nucleotide is observed in a collection of sequence reads.

The term "nucleosome-free fragments," as used herein, refers to fragments of genomic DNA that are relatively depleted or devoid of nucleosomes, i.e., between nucleosomes.

The term "chromatin accessibility," as used herein, refers to how accessible a nucleic acid site is within a polynucleotide, such as in genomic DNA, i.e., how "open" the chromatin is. A nucleic acid site associated with a polypeptide, such as with genomic DNA in nucleosomes, is usually inaccessible. A nucleic acid site not complexed with a polypeptide is generally accessible, such as with genomic DNA between nucleosomes (with the exception of nucleic acid sites complexed with transcription factors and other DNA binding proteins).

The term "DNA binding protein occupancy," as used herein, refers to whether a binding site for a sequence specific DNA binding protein (e.g., a binding site for a transcription factor) is occupied by the DNA binding protein. DNA binding protein occupancy can be measured quantitatively or qualitatively.

The term "global occupancy," as used herein, refers to whether a plurality of different binding sites for a DNA binding protein that are distributed throughout the genome (e.g., a binding sites for a transcription factor) are bound by the DNA binding protein. DNA binding protein occupancy can be measured quantitatively or qualitatively.

The term "diagnosis," as used herein, refers to a determination of whether a subject has a particular disease or condition.

The term "prognosis," as used herein, refers to prediction of a clinical outcome, e.g., disease recurrence, recovery from a disease, death, as well as a prediction of how a subject that has a particular disease or condition will respond to a particular treatment.

Other definitions of terms may appear throughout the specification.

DESCRIPTION OF EXEMPLARY EMBODIMENTS

In one aspect, a method for analyzing chromatin is provided. In certain embodiments, the method comprises: (a) treating chromatin isolated from a population of cells with an insertional enzyme complex to produce tagged fragments of genomic DNA. In this step, the chromatin is tagmented (i.e., cleaved and tagged in the same reaction) using an insertional enzyme such as Tn5 or MuA that cleaves the genomic DNA in open regions in the chromatin and adds adaptors to both ends of the fragments. Methods for tagmenting isolated genomic DNA are known in the art (see, e.g., Caruccio Methods Mol. Biol. 2011 733: 241-55; Kaper et al, Proc. Natl. Acad. Sci. 2013 110: 5552-7; Marine et al, Appl. Environ. Microbiol. 2011 77: 8071-9 and US20100120098) and are commercially available from Illumina (San Diego, Calif.) and other vendors. Such systems may be readily adapted for use herein. In some cases, the conditions may be adjusted to obtain a desirable level of insertion in the chromatin (e.g., an insertion that occurs, on average, every 50 to 200 base pairs in open regions). The chromatin used in the method may be made by any suitable method. In some embodiments, nuclei may be isolated, lysed, and the chromatin may be further purified, e.g., from the nuclear envelope. In other embodiments, the chromatin may be isolated by contacting isolated nuclei with the reaction buffer. In these embodiments, the isolated nuclei may lyse when it makes contact with the reaction buffer (which comprises insertional enzyme complexes and other necessary reagents), which allows the insertional enzyme complexes access to the chromatin. In these embodiments, the method may comprise isolating nuclei from a population of cells; and combining the isolated nuclei with the transposase and adaptors, wherein the combining results in both lysis of the nuclei to release said chromatin and production of the adaptor-tagged fragments of genomic DNA. The chromatin does not require cross-linking as in other methods (e.g., ChIP-SEQ methods).

After the chromatin has been fragmented and tagged to produce tagged fragments of genomic DNA, at least some of the adaptor tagged fragments are sequenced to produce a plurality of sequence reads. The fragments may be sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513: 19-39) and Morozova et al (Genomics. 2008 92:255-64), which are incorporated by reference for the general descriptions of the methods and the particular steps of the methods, including all starting products, methods for library preparation, reagents, and final products for each of the steps. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. In certain cases, the primers used may contain a molecular barcode (an "index") so that different pools can be pooled together before sequencing, and the sequence reads can be traced to a particular sample using the barcode sequence.

In another aspect, the present disclosure provides a method for determining accessibility of a polynucleotide at a site, wherein the polynucleotide is from a cell sample, said method comprising: inserting a plurality of molecular tags with an insertional enzyme into the polynucleotide and using the molecular tags to determine accessibility at the site. The cell sample can be from a primary source. The cell sample may consist of a single cell. The cell sample may consist of a finite number of cells (e.g. less than about 500,000 cells).

The method can further comprise using the determined accessibility to identify one or more proteins that are bound to the polynucleotide at the site. In some instances, at least one of the proteins is a transcription factor. Additionally, the method can comprise using the molecular tags to generate an accessibility map of the polynucleotide.

The polynucleotide may be fragmented into a plurality of fragments during the insertion of the molecular tags. In some cases, the fragments may be amplified. In some cases, the fragments can be sequenced to generate a plurality of sequencing reads. This may be used to determine the accessibility of the polynucleotide at any given site. The fragments may be sequenced using a high-throughput sequencing technique. In some cases, the sequencing reads can be normalized based on the sequence insertion preference of the insertional enzyme. The length of the sequenced reads can be used to determine a chromatin state annotation.

The polynucleotide can be bound to a plurality of association molecules. The association molecules can be, for example, proteins, nucleic acids or saccharides. In some cases, the association molecules can comprise histones. In other cases, the association molecules can comprise aptamers.

The insertional enzyme can be any enzyme capable of inserting a nucleic acid sequence into a polynucleotide. In some cases, the insertional enzyme can insert the nucleic acid sequence into the polynucleotide in a substantially sequence-independent manner. The insertional enzyme can be prokaryotic or eukaryotic. Examples of insertional enzymes include, but are not limited to, transposases, HERMES, and HIV integrase. The transposase can be a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Te1, THE-1, Tn/O, TnA, Tn3, Tn5, Tn7, Tn10, Tn552, Tn903, Tol1, Tol2, TnlO, Tyl, any prokaryotic transposase, or any transposase related to and/or derived from those listed above. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. In some cases, the insertion can be facilitated and/or triggered by addition of one or more cations. The cations can be divalent cations such as, for example, $Ca^{2+}$, $Mg^{2+}$ and $Mn^{2+}$.

The molecular tags can comprise sequencing adaptors, locked nucleic acids (LNAs), zip nucleic acids (ZNAs), RNAs, affinity reactive molecules (e.g. biotin, dig), self-complementary molecules, phosphorothioate modifications, azide or alkyne groups. In some cases, the sequencing adaptors can further comprise a barcode label. Further, the barcode labels can comprises a unique sequence. The unique sequences can be used to identify the individual insertion events. Any of the tags can further comprise fluorescence tags (e.g. fluorescein, rhodamine, Cy3, Cy5, thiazole orange, etc.).

Additionally, the insertional enzyme can further comprise an affinity tag. In some cases, the affinity tag can be an antibody. The antibody can bind to, for example, a transcription factor, a modified nucleosome or a modified nucleic acid. Examples of modified nucleic acids include, but are not limited to, methylated or hydroxymethylated DNA. In other cases, the affinity tag can be a single-stranded nucleic acid (e.g. ssDNA, ssRNA). In some examples, the single-stranded nucleic acid can bind to a target nucleic acid. In further cases, the insertional enzyme can further comprise a nuclear localization signal.

In some cases, the cell sample can be permeabilized to allow access for the insertional enzyme. The permeabilization can be performed in a way to minimally perturb the nuclei in the cell sample. In some instances, the cell sample can be permeabilized using a permeabilization agent. Examples of permeabilization agents include, but are not limited to, NP40, digitonin, tween, streptolysin, and cationic lipids. In other instances, the cell sample can be permeabilized using hypotonic shock and/or ultrasonication. In other cases, the insertional enzyme can be highly charged, which may allow it to permeabilize through cell membranes.

In yet another aspect, the present disclosure provides a method for analyzing the three-dimensional structure of a polynucleotide from a cell sample, comprising: inserting a plurality of molecular tags with an insertional enzyme into the polynucleotide; and using the molecular tags to analyze the three-dimensional structure of the polynucleotide. The insertional enzyme can comprise two or more enzymatic moieties, which may be optionally linked together. The enzymatic moieties can be linked by using any suitable chemical synthesis or bioconjugation methods. For example, the enzymatic moieties can be linked via an ester/amide bond, a thiol addition into a maleimide, Native Chemical Ligation (NCL) techniques, Click Chemistry (i.e. an alkyne-azide pair), or a biotin-streptavidin pair. In some cases, each of the enzymatic moieties can insert a common sequence into the polynucleotide. The common sequence can comprise a common barcode. The enzymatic moieties can comprise transposases or derivatives thereof. In some embodiments, the polynucleotide may be fragmented into a plurality of fragments during the insertion. The fragments comprising the common barcode can be determined to be in proximity in the three-dimensional structure of the polynucleotide.

The polynucleotide can be genomic DNA. The polynucleotide can be further bound to proteins, such as histones, and may be optionally packaged in the form of chromatin. In particular cases, DNA fragments corresponding to one or more regions of a genome (e.g., 2 or more, 10 or more, 50 or more, 100 or more, up to 1,000 or more regions) may be enriched, i.e., selected, by hybridization prior to sequencing. In these embodiments, the entire library does not need to be sequenced. Depending on the desired result and length of the selected region (if a selection step has been performed), this step of the method may result in at least 1,000 sequencing (e.g., at least 10,000, at least 100,000, at least 500,000, at least $10^6$, at least $5\times10^6$, up to $10^7$ or more sequencing reads). The sequence reads are generally stored in computer memory.

Some embodiments of the methods involve making an epigenetic map of a region of the genome of the cells. This step may be done by mapping information obtained from the sequence reads to the region. In these embodiments, the sequence reads are analyzed computationally to produce a number of numerical outputs that are mapped to a representation (e.g., a graphical representation) of a region of interest. As will be explained in greater detail below, many types of information may be mapped, including, but not limited to: (i) cleavage sites for the transposase; (ii) the sizes of the fragments produced in step a); (iii) fragment length; (iii) the positions of sequence reads of a defined range in length; and (iv) sequence read abundance.

For example, the sequence reads may be analyzed computationally to identify the ends of the fragments (from which the transposon cleavage sites can be inferred). In these embodiments, one end of a fragment can be defined by sequence that is at the beginning of a sequencing read and the other end of the fragment can be defined by sequence that is at the beginning of a second sequencing read, where the first and second sequencing reads were obtained by paired end sequencing (e.g., using Illumina's sequencing platform). The same information can be obtained from examining the beginning and end of longer sequence reads (which should, in theory, have the sequence of both adaptors; one at one end and the other at the other end). In these embodiments, a single sequence read may contain both adaptor sequences, in which case both ends of a fragment (which correspond to two cleavage sites for the two separate transposases) can be inferred from a single sequence read. The lengths of the fragments can be calculated by, e.g., mapping the fragment ends onto the nucleotide sequence of the region of interest, and counting the number of base pairs between those positions. The information used may be obtained using the nucleotide sequences at the beginning and/or the end of a sequence read.

In certain cases, the sequence reads can be placed into groups by length. In some embodiments, some sequences can be annotated as being a nucleosome-free sequence (i.e., a sequence from a fragment that is predicted to be between nucleosomes) based on its size. Reads that are associated with mononucleosomes, dinucleosomes and trinucleosomes can also be identified. These cutoffs can be determined using the data shown in FIG. 12. Fragment lengths (which provide the same information as sequence read lengths) can also be processed in the same way. In certain cases, sequence read abundance, i.e., the number of times a particular sequence in a genomic region is represented in the sequence reads, may be calculated.

The resultant epigenetic map can provide an analysis of the chromatin in the region of interest. For example, depending on which information is mapped, the map can show one or more of the following: a profile of chromatin accessibility along the region; DNA binding protein (e.g., transcription factor) occupancy for a site in the region; nucleosome-free DNA in the region; positioning of nucleosomes along the region; and a profile of chromatin states along the region. In some embodiments, the method may further comprise measuring global occupancy of a binding site for the DNA binding protein by, e.g., aggregating data for one DNA binding protein over a plurality of sites to which that protein binds. In certain instances, the map can also be annotated with sequence information, and information about the sequence (e.g., the positions of promoters, introns, exons, known enhancers, transcriptional start sites, untranslated regions, terminators, etc.) so that the epigenetic information can be viewed in context with the annotation.

In certain embodiments, the epigenetic map can provide information regarding active regulatory regions and/or the transcription factors that are bound to the regulatory regions. For example, nucleosome positions can be inferred from the lengths of sequencing reads generated. Alternatively, transcription factor binding sites can be inferred from the size, distribution and/or position of the sequencing reads generated. In some cases, novel transcription factor binding sites can be inferred from sequencing reads generated. In other cases, novel transcription factors can be inferred from sequencing reads generated.

The population of cells used in the assay may be composed of any number of cells, e.g., about 500 to about $10^6$ or more cells, about 500 to about 100,000 cells, about 500 to about 50,000 cells, about 500 to about 10,000 cells, about 50 to 1000 cells, about 1 to 500 cells, about 1 to 100 cells, about 1 to 50 cells, or a single cell. In some cases, the cell sample can consist of less than about 1000, about 2000, about 3000, about 4000, about 5000, about 6000, about 7000, about 8000, about 9000, about 10,000, about 15,000, about 20,000, about 25,000, about 30,000, about 40,000, about 50,000, about 60,000, about 70,000, about 80,000, about 90,000, about 100,000, about 120,000, about 140,000, about 160,000, about 180,000, about 200,000, about 250,000, about 300,000, about 350,000, about 400,000, about 450,000, about 500,000, about 600,000, about 700,000, about 800,000, about 900,000, or about 1,000,000 cells. In other cases, the cell sample can consist of more than about 1000, about 2000, about 3000, about 4000, about 5000, about 6000, about 7000, about 8000, about 9000, about 10,000, about 15,000, about 20,000, about 25,000, about 30,000, about 40,000, about 50,000, about 60,000, about 70,000, about 80,000, about 90,000, about 100,000, about 120,000, about 140,000, about 160,000, about 180,000, about 200,000, about 250,000, about 300,000, about 350,000, about 400,000, about 450,000, about 500,000, about 600,000, about 700,000, about 800,000, about 900,000, or about 1,000,000 cells.

The cells can be from any source. In certain cases, the cells may be obtained from a culture of cells, e.g., a cell line. In other cases, the cells may be isolated from an individual (e.g., a patient or the like). The cells may be isolated from a soft tissue or from a bodily fluid, or from a cell culture that is grown in vitro. In particular embodiments, the chromatin may be isolated from a soft tissue such as brain, adrenal gland, skin, lung, spleen, kidney, liver, spleen, lymph node, bone marrow, bladder stomach, small intestine, large intestine or muscle, etc. Bodily fluids include blood, plasma, saliva, mucous, phlegm, cerebral spinal fluid, pleural fluid, tears, lactal duct fluid, lymph, sputum, cerebrospinal fluid, synovial fluid, urine, amniotic fluid, and semen, etc.

In some embodiments, the polynucleotide (e.g. genomic DNA, chromosomal DNA) used in the method may be from blood cells, wherein blood cells refers to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocytes, eosinophils, basophils and monocytes). These five types of white blood cells can be further divided into two groups, granulocytes (which are also known as polymorphonuclear leukocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. Other cells are present in blood that can be isolated. If blood is first contacted with an agent and then a sample of the blood is used in an assay, then a portion or all of the contacted blood may be used in the assay.

In certain embodiments, the cell sample can be isolated directly from a primary source. For example, the cell sample can be isolated directly from fresh tissues. In other cases, the cell sample can be isolated directly from frozen tissues. In yet other cases, the cell sample can be isolated directly from fixed tissues. Further examples of primary sources of cell samples include, but are not limited to, cells dissociated from tissues, blood cells, FFPE tissues, bacterial, viral, mitochondria, chloroplast, in vitro assembled protein DNA complexes, neutrophil extracellular traps.

Using the methods provided in the present disclosure, the disease state in a subject can be analyzed based on the accessibility of a polynucleotide site in a cell sample obtained from the subject. For example, transcription factor occupancy at any given site can result in the lack of accessibility at the site. Based on the transcription factor occupancy, the subject can then be treated with a suitable agent (e.g. a transcription factor inhibitor).

In certain cases, the cell samples can be further analyzed phenotypically. For example, the cell samples can be analyzed using fluorescence activated cell sorting (FACS) and/or laser capture microdissection (LCM). In some cases, the cell sample and/or polynucleotides may be divided into a plurality of portions. The portions can be divided based on the molecular tags (e.g. fluorescence tags). In some cases, the cell sample and/or polynucleotides can be sorted. The sorting can be performed after the molecular tags are inserted into the polynucleotide. The sorting can be performed before the fragments are sequenced. The gene transcription of the cell samples can also be analyzed using techniques such as fluorescence in situ hybridization (FISH). The chromatin accessibility can be correlated with the phenotypical, transcriptional or translational analysis.

In some embodiments, the cells are of the same cell type. In these embodiments, the population of cells may be selected by MACS or FACS from a heterogeneous population of cells, e.g., blood, by known methods using labeled antibodies to cells surface markers. A wide variety of cells can be isolated using these methods, including stem cells, cancer stem cells and subsets of blood cells. In particular embodiments the following cells may be isolated from blood by FACS or MACS; T cells ($CD3^+$ $CD4^+$ $CD8^+$), B cells ($CD19^+$ $CD20^+$), dendritic cells ($CD11c^+$ $CD20^+$), NK Cell ($CD56^+$), stem cells/precursor cells ($CD34^+$; hematopoietic stem cells only), macrophage/monocytes (CD14+ $CD33^+$), granulocytes ($CD66b^+$), platelet ($CD41^+$ $CD61^+$ $CD62^+$), erythrocytes ($CD235a^+$), endothelial cells ($CD146^+$) and epithelial cells ($CD326^+$). Subsets of these cells can be isolated using antibodies to further cell surface markers.

In some embodiments, the method can be used to compare two samples. In these embodiments, the method may comprise analyzing a first population of cells using the above-described method to produce a first epigenetic map; and analyzing a second population of cells using the above-described method to produce a second epigenetic map; and comparing the first epigenetic map to the second epigenetic map, e.g., to see if there are any changes in chromatin openness or transcription factor occupancy, for example.

In some embodiments, the first population of cells and the second population of cells are collected from the same individual at different times. In other embodiments, the first population of cells and the second population of cells are different populations of cells collected from tissues or different individuals.

Exemplary cell types that can be used in the method include, for example, cells isolated from a tissue biopsy (e.g., from a tissue having a disease such as colon, breast, prostate, lung, skin cancer, or infected with a pathogen etc.) and normal cells from the same tissue, e.g., from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and normal cells (e.g., cells that are otherwise identical to the experimental cells except that they are not immortalized, infected, or treated, etc.); cells isolated from a mammal with a cancer, a disease, a geriatric mammal, or a mammal exposed to a condition, and cells from a mammal of the same species, e.g., from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be compared. In another embodiment, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells. Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

In some exemplary embodiments, the method may be used to identify the effect of a test agent, e.g., a drug, or to determine if there are differences in the effect of two or more different test agents. In these embodiments, two or more identical populations of cells may be prepared and, depending on how the experiment is to be performed, one or more of the populations of cells may be incubated with the test agent for a defined period of time. After incubation with the test agent, the chromatin of the populations of cells can be analyzed using the methods set forth above, and the results can be compared. In a particular embodiment, the cells may be blood cells, and the cells can be incubated with the test agent ex vivo. These methods can be used to determine the mode of action of a test agent, to identify changes in chromatin structure or transcription factor occupancy in response to the drug, for example.

The method described above may also be used as a diagnostic (which term is intended to include methods that provide a diagnosis as well as methods that provide a prognosis). These methods may comprise, e.g., analyzing chromatin from a patient using the method described above to produce an epigenetic map; and providing a diagnosis or prognosis based on the epigenetic map.

The method set forth herein may be used to provide a reliable diagnostic to any condition associated with altered chromatin or DNA binding protein occupancy. The method can be applied to the characterization, classification, differentiation, grading, staging, diagnosis, or prognosis of a condition characterized by an epigenetic pattern (e.g., a pattern of chromatin accessibility or DNA binding protein occupancy). For example, the method can be used to determine whether the epigenetic map of a sample from an individual suspected of being affected by a disease or condition is the same or different compared to a sample that is considered "normal" with respect to the disease or condition. In particular embodiments, the method can be directed to diagnosing an individual with a condition that is characterized by an epigenetic pattern at a particular locus in a test sample, where the pattern is correlated with the condition. The methods can also be used for predicting the susceptibility of an individual to a condition.

Exemplary conditions that are suitable for analysis using the methods set forth herein can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

In some embodiments, the method can provide a prognosis, e.g., to determine if a patient is at risk for recurrence. Cancer recurrence is a concern relating to a variety of types of cancer. The prognostic method can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The method can also be used to determining a proper course of treatment for a patient having a disease or condition, e.g., a patient that has cancer. A course of treatment refers to the therapeutic measures taken for a patient after diagnosis or after treatment. For example, a determination of the likelihood for recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

In a particular embodiment, a lab will receive a sample (e.g., blood) from a remote location (e.g., a physician's office or hospital), the lab will analyze cells in the sample as described above to produce data, and the data may be forwarded to the remote location for analysis.

Compositions

In one aspect, the present disclosure provides compositions related to the methods provided herein. The composition can comprise a polynucleotide, an insertional enzyme and an insert element, wherein: the insert element can comprise a nucleic acid comprising a predetermined sequence and the insertional enzyme can further comprise an affinity tag. The polynucleotide can be further bound to a plurality of association molecules. The association molecules can be proteins (e.g. histones) or nucleic acids (e.g. aptamers). The affinity tag can be an antibody. In some cases, the antibody can be bound to a transcription factor. In other cases, the antibody can be bound to a modified nucleosome. In further cases, the antibody can be bound to a modified nucleic acid. Examples of modified nucleic acids include, but are not limited to, methylated or hydroxymethylated DNA. The affinity tag can also be a single-stranded nucleic acid (e.g. ssDNA, ssRNA). In some cases, the single-stranded nucleic acid can be bound to a target nucleic acid. In some instances, the insertional enzyme can further comprise a nuclear localization signal.

The composition can comprise a polynucleotide, an insertional enzyme and an insert element, wherein: the insertional enzyme comprises two or more enzymatic moieties and the enzymatic moieties are linked together. The insert element can be bound to the insertional enzyme. The insertional enzyme can also be bound to the polynucleotide. In some cases, the polynucleotide can be further bound to a plurality of association molecules. The association molecules can be proteins (e.g. histones) or nucleic acids (e.g. aptamers).

Kits

In yet another aspect, the present disclosure provides kits that contain reagents for practicing the subject methods, as described above. The subject kits can comprise: (a) reagents for isolating nuclei from a population of cells; (b) transposase and transposon tags, and (c) transposase reaction buffer, wherein the components of the kit are configured such that, combining the reaction buffer, transposase and adaptors with nuclei in vitro results in both lysis of the nuclei to release chromatin and production of adaptor-tagged fragments of genomic DNA.

In some cases, the kit can comprise: (a) a cell lysis buffer; (b) an insertional enzyme comprising an affinity tag; and (c) an insert element comprising a nucleic acid, wherein said nucleic acid comprises a predetermined sequence. The insertional enzyme can be, for example, a transposase. The insertional enzyme can also comprise two or more enzymatic moieties that are linked together. In some cases, the affinity tag can be an antibody. The antibody can bind to a transcription factor, a modified nucleosome, or a modified nucleic acid. Examples of modified nucleic acids include, but are not limited to, methylated or hydroxymethylated DNA. In other cases, the affinity tag can be a single-stranded nucleic acid (e.g. ssDNA, ssRNA).

The kit may optionally contain other components, for example: PCR primers, PCR reagents such as polymerase, buffer, nucleotides etc., as described above. The various components of the kit may be present in separate containers or certain compatible components may be precombined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Embodiments

A method of mapping chromatin is provided. In some embodiments, this method comprises the steps of: fragmenting the chromatin of rare or abundant cells with a transposase which inserts sequencing adapters into the polynucleotides within the chromatin, and amplifying and sequencing the fragments to generate a cell-specific map.

In certain embodiments, the cell-specific map provides information regarding active regulatory regions and the transcription factors that are bound to said regulatory regions.

In certain embodiments, the number of said rare cells is between 1 and 100,000.

In certain embodiments, the transposase is derived from Tn5 transposase.

In certain embodiments, the transposase is derived from MuA transposase.

In certain embodiments, nucleosome positions are inferred from the lengths of sequencing reads generated.

In certain embodiments, transcription factor binding sites are inferred from sequencing reads generated.

In certain embodiments, chromatin is isolated directly from fresh tissues.

In certain embodiments, chromatin is isolated directly from frozen tissues.

In certain embodiments, chromatin is isolated directly from fixed tissues.

In certain embodiments, sequences are added to the sequencing adapter to uniquely identify the fragments for multiplexing (barcoding).

In certain embodiments, an affinity tag is used to target the transposase to a specific macromolecule of interest.

In certain embodiments, sequences are added to the sequencing adapter to uniquely identify the fragments for multiplexing (barcoding), and an affinity tag is used to target the transposase to a specific macromolecule of interest.

In certain embodiments the affinity tag is an antibody targeted to a transcription factor.

In certain embodiments the affinity tag is an antibody targeted to a modified nucleosome.

In certain embodiments, the insert size distribution at a specific genomic locus is used to infer chromatin openness.

In certain embodiments, the insert size distribution and positions of insertion are used to infer transcription factor binding.

In certain embodiments, the number of sequencing reads obtained is normalized by measured sequence insertion preference of the transposase.

In certain embodiments, novel transcription factor binding sites are inferred from sequencing reads generated.

In certain embodiments, novel transcription factors are inferred from sequencing reads generated.

In certain embodiments, causal variants can be inferred by looking at allele specific generation of sequencing reads.

In certain embodiments, chromatin state annotations are inferred from the distribution of lengths of sequencing reads.

EXAMPLES

Aspects of the present teachings can be further understood in light of the following examples, which should not be construed as limiting the scope of the present teachings in any way.

Example 1. Assay for Transposase Accessible Chromatin Using Sequencing (ATAC-Seq)

Described herein is an Assay for Transposase Accessible Chromatin using sequencing (ATAC-seq)—based on direct in vitro transposition of sequencing adapters into native chromatin—as a rapid and sensitive method for integrative epigenomic analysis. ATAC-seq captures open chromatin sites using a simple 2-step protocol from 500 to 50,000 cells, and reveals the interplay between genomic locations of open chromatin, DNA binding proteins, individual nucleosomes, and higher-order compaction at regulatory regions with nucleotide resolution. Classes of DNA binding factor that strictly avoid, can tolerate, or tend to overlap with nucleosomes have been discovered. Using ATAC-seq, the serial daily epigenomes of resting human T cells was measured and evaluated from a proband via standard blood draws, demonstrating the feasibility of reading personal epigenomes in clinical timescales for monitoring health and disease.

Materials and Methods

An exemplary implementation of ATAC-seq protocol has three major steps:

1) Prepare nuclei: To prepare nuclei, 50,000 cells were spun at 500×g for 5 minutes, followed by a wash using 50 µL of cold 1×PBS and centrifugation at 500×g for 5 minutes. Cells were lysed using cold lysis buffer (10 mM Tris-Cl, pH 7.4, 10 mM NaCl, 3 mM $MgCl_2$ and 0.1% IGEPAL CA-630) Immediately after lysis, nuclei were spun at 500×g for 10 minutes using a refrigerated centrifuge. To avoid losing cells during the nuclei prep, a fixed angle centrifuge was used and they were carefully pipetted away from the pellet after centrifugations.

2) Transpose and purify Immediately following the nuclei prep, the pellet was resuspended in the transposase reaction mix (25 µL 2×TD buffer, 2.5 µL Transposase (Illumina) and 22.5 µL of nuclease free water). The transposition reaction was carried out for 30 minutes at 37° C. Directly following transposition the sample was purified using a Qiagen Minelute kit.

3) PCR: Following purification, we amplified library fragments using 1×NEBnext PCR master mix and 1.25 µM of custom Nextera PCR primers 1 and 2 (see table below), using the following PCR conditions: 72° C. for 5 minutes, 98° C. for 30 seconds, followed by thermocycling at 98° C. for 10 seconds, 63° C. for 30 seconds and 72° C. for 1 minute. To reduce GC and size bias in PCR, the PCR reactions were monitored using qPCR in order to stop amplification prior to saturation. To do this, the full libraries were amplified for 5 cycles, after 5 cycles an aliquot of the PCR reaction was taken and added to 10 µl of the PCR cocktail with Sybr Green at a final concentration of 0.6×. We ran this reaction for 20 cycles, to determine the additional number of cycles needed for the remaining 45 µL reaction. The libraries were purified using a Qiagen PCR cleanup kit yielding a final library concentration of ~30 nM in 20 µL. Libraries were amplified for a total of 10-12 cycles.

```
Ad1_noMX:        AATGATACGGCGACCACCGAGATCTACACTCGTCGGCAGCGTCAGATGTG
                 (SEQ ID NO: 1)

Ad2.1_TAAGGCGA   CAAGCAGAAGACGGCATACGAGATTCGCCTTAGTCTCGTGGGCTCGGAGATGT
                 (SEQ ID NO: 2)

Ad2.2_CGTACTAG   CAAGCAGAAGACGGCATACGAGATCTAGTACGGTCTCGTGGGCTCGGAGATGT
                 (SEQ ID NO: 3)

Ad2.3_AGGCAGAA   CAAGCAGAAGACGGCATACGAGATTTCTGCCTGTCTCGTGGGCTCGGAGATGT
                 (SEQ ID NO: 4)

Ad2.4_TCCTGAGC   CAAGCAGAAGACGGCATACGAGATGCTCAGGAGTCTCGTGGGCTCGGAGATGT
                 (SEQ ID NO: 5)

Ad2.5_GGACTCCT   CAAGCAGAAGACGGCATACGAGATAGGAGTCCGTCTCGTGGGCTCGGAGATGT
                 (SEQ ID NO: 6)

Ad2.6_TAGGCATG   CAAGCAGAAGACGGCATACGAGATCATGCCTAGTCTCGTGGGCTCGGAGATGT
                 (SEQ ID NO: 7)

Ad2.7_CTCTCTAC   CAAGCAGAAGACGGCATACGAGATGTAGAGAGGTCTCGTGGGCTCGGAGATGT
                 (SEQ ID NO: 8)

Ad2.8_CAGAGAGG   CAAGCAGAAGACGGCATACGAGATCCTCTCTGGTCTCGTGGGCTCGGAGATGT
                 (SEQ ID NO: 9)

Ad2.9_GCTACGCT   CAAGCAGAAGACGGCATACGAGATAGCGTAGCGTCTCGTGGGCTCGGAGATGT
                 (SEQ ID NO: 10)

Ad2.10_CGAGGCTG  CAAGCAGAAGACGGCATACGAGATCAGCCTCGGTCTCGTGGGCTCGGAGATGT
                 (SEQ ID NO: 11)

Ad2.11_AAGAGGCA  CAAGCAGAAGACGGCATACGAGATTGCCTCTTGTCTCGTGGGCTCGGAGATGT
                 (SEQ ID NO: 12)

Ad2.12_GTAGAGGA  CAAGCAGAAGACGGCATACGAGATTCCTCTACGTCTCGTGGGCTCGGAGATGT
                 (SEQ ID NO: 13)

Ad2.13_GTCGTGAT  CAAGCAGAAGACGGCATACGAGATATCACGACGTCTCGTGGGCTCGGAGATGT
                 (SEQ ID NO: 14)

Ad2.14_ACCACTGT  CAAGCAGAAGACGGCATACGAGATACAGTGGTGTCTCGTGGGCTCGGAGATGT
                 (SEQ ID NO: 15)

Ad2.15_TGGATCTG  CAAGCAGAAGACGGCATACGAGATCAGATCCAGTCTCGTGGGCTCGGAGATGT
                 (SEQ ID NO: 16)

Ad2.16_CCGTTTGT  CAAGCAGAAGACGGCATACGAGATACAAACGGGTCTCGTGGGCTCGGAGATGT
                 (SEQ ID NO: 17)

Ad2.17_TGCTGGGT  CAAGCAGAAGACGGCATACGAGATACCCAGCAGTCTCGTGGGCTCGGAGATGT
                 (SEQ ID NO: 18)

Ad2.18_GAGGGGTT  CAAGCAGAAGACGGCATACGAGATAACCCCTCGTCTCGTGGGCTCGGAGATGT
                 (SEQ ID NO: 19)
```

```
Ad2.19_AGGTTGGG  CAAGCAGAAGACGGCATACGAGATCCCAACCTGTCTCGTGGGCTCGGAGATGT
                 (SEQ ID NO: 20)

Ad2.20_GTGTGGTG  CAAGCAGAAGACGGCATACGAGATCACCACACGTCTCGTGGGCTCGGAGATGT
                 (SEQ ID NO: 21)

Ad2.21_TGGGTTTC  CAAGCAGAAGACGGCATACGAGATGAAACCCAGTCTCGTGGGCTCGGAGATGT
                 (SEQ ID NO: 22)

Ad2.22_TGGTCACA  CAAGCAGAAGACGGCATACGAGATTGTGACCAGTCTCGTGGGCTCGGAGATGT
                 (SEQ ID NO: 23)

Ad2.23_TTGACCCT  CAAGCAGAAGACGGCATACGAGATAGGGTCAAGTCTCGTGGGCTCGGAGATGT
                 (SEQ ID NO: 24)

Ad2.24_CCACTCCT  CAAGCAGAAGACGGCATACGAGATAGGAGTGGGTCTCGTGGGCTCGGAGATGT
                 (SEQ ID NO: 25)
```

Low cell number protocol: To prepare the 500 and 5,000 cell reactions the same protocol was used with some notable exceptions: The transposition reaction was done in a 5 µL instead of 50 µL reaction. Also, the Qiagen Minelute purification was eliminated prior to PCR and instead took the 5 µL reaction immediately after transposition directly into the 50 µL PCR.

Library QC and quantitation: During the ATAC-seq protocol, the size selection step was avoided to maximize the library complexity. The sequenced insert size is a distribution between 40 bp to 1 kb with a mean of ~120 bps. From bioanalyzer and gels we observed fragments >2 kb, which would make Qubit and other mass-based quantitation methods hard to interpret. For this reason we quantified our libraries using qPCR based methods.

$CD4^+$ enrichment from peripheral blood: One green-top tube of whole blood was obtained from 1 normal volunteer three times over a 72-hour period, under a Stanford University IRB-approved protocol. Informed consent was obtained. 5 mL of blood at each timepoint was negatively selected for CD4+ cells, using RosetteSep Human $CD4^+$ T Cell Enrichment Cocktail (StemCell Technology). RosetteSep cocktail was incubated with the blood at 50 µL/mL for 20 min, diluted in an equal volume of PBS with 2% FBS, and underlayed with 15 mL Ficol-Paque Plus (GE). Blood was centrifuged for 20 minutes at 1200×g without break, negatively selected cells were removed from the density medium: plasma interface, and cells were washed X2 in PBS with 2% FBS.

FACS sorting peripheral blood leukocytes and GM cells: GM 12878 cells were stained with DAPI NucBlue Fixed Cell Stain (molecular probes) and live cells were sorted using a FACSAria (BD Biosciences) using a 100 µm nozzle. One peripheral blood sample (buffy coat) was stained with BD Bioscience antibodies CD14-A-488 (M5E2, 1:20), CD3-PE-Cy7 (SK7, 1:20), CD4-APC-Cy7 (RPA-T4, 1:20), and CD8 (RPA-T8, 1:20) for 20 minutes in the dark at RT. Cells were lysed using BDpharmLyse 1:10 dil in diH20 (BD) for 15 min, centrifuged for 5 minutes, washed with PBS 2% FBS×2, and resuspended in PBS with 2% FBS. 50,000 $CD3^+CD8^+$, $CD3^+CD4^+$, and $CD14^+$ cell populations were sorted into PBS with 10% FBS.

Data Analysis

Primary data processing: Data was collected using either 34×8×34 reads from a MiSeq or 50×8×50 reads on a HiSeq. Reads were aligned to hg19 using BOWTIE (Langmead et al Genome Biol. 2009 10, R25) using the parameters −X2000 and −m1. These parameters ensured that fragments up to 2 kb were allowed to align (−X2000) and that only unique aligning reads were collected (−m1). For all data files duplicates were removed using Picard.

For peak calling and footprinting, the read start sites were adjusted to represent the center of the transposon binding event. Previous descriptions of the Tn5 transposase show that the transposon binds as a dimer and inserts two adapters separated by 9 bps (Adey, A. et al. Genome Biol 2010 11: R119). Therefore, all reads aligning to the + strand were offset by +4 bps, and all reads aligning to the − strand were offset −5 bps.

ATAC-seq peak calling: We used ZINBA to call all reported ATAC-seq peaks in this manuscript. ZINBA was run using a window size of 300 bp and an offset 75 bp. Alignability was used to model the zero-inflated component and the ATAC-seq read count for the background and enriched components. Enriched regions were identified as those with a posterior probability >0.8.

ATAC-seq insertion size enrichment analysis within chromatin annotations: First, the distribution of paired-end sequencing fragment sizes overlapping each chromatin state (see the ensemble.org website) were computed. The distributions were then normalized to the percent maximal within each state and enrichment was computed relative to the genome-wide set of fragment sizes.

Figure 3A:
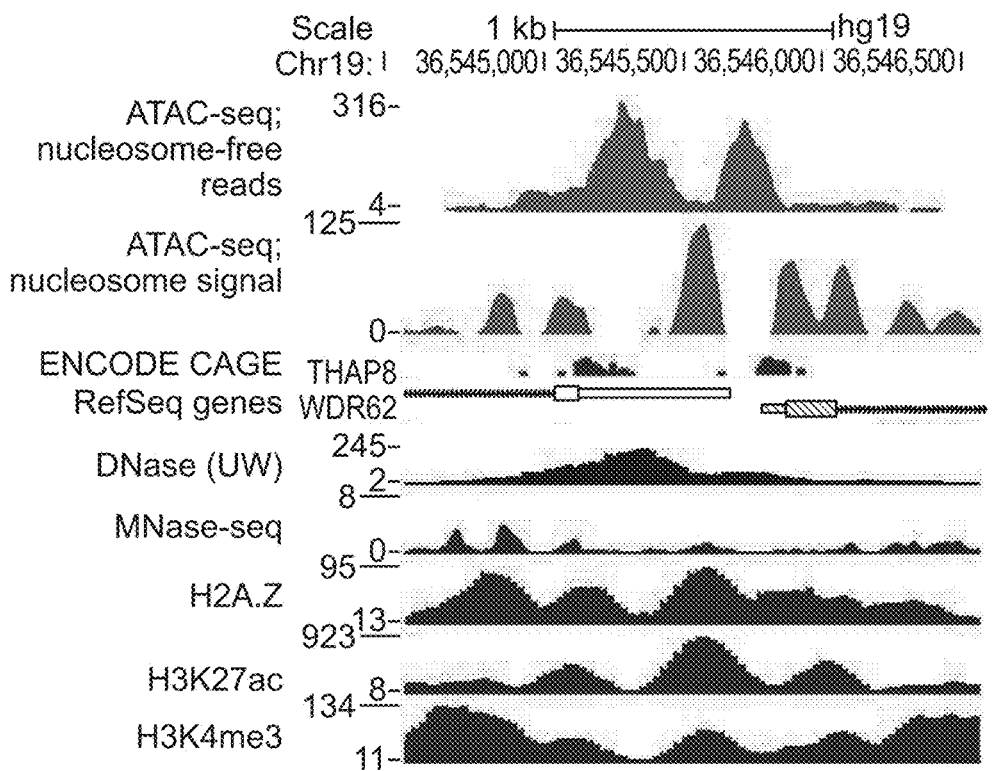
FIGS. 3A-3E: ATAC-seq provides genome-wide information on nucleosome positioning in regulatory regions. (a) An example locus containing two transcription start sites (TSSs) showing nucleosome free read track, calculated nucleosome track (Methods), as well as DNase, MNase, and H3K27ac, H3K4me3, and H2A.Z tracks for comparison. (b) ATAC-seq (198 million paired reads) and MNase-seq (4 billion single-end reads from ref 23) nucleosome signal shown for all active TSSs (n=64,836), TSSs are sorted by CAGE expression. (c) TSSs are enriched for nucleosome free fragments, and show phased nucleosomes similar to those seen by MNase-seq at the −2, −1, +1, +2, +3 and +4 positions. (d) Relative fraction of nucleosome associated vs. nucleosome free (NFR) bases in TSS and distal sites (see Methods). (e) Hierarchical clustering of DNA binding factor position with respect to the nearest nucleosome dyad within accessible chromatin reveals distinct classes of DNA binding factors. Factors strongly associated with nucleosomes are enriched for chromatin remodelers.
Figure 3B:
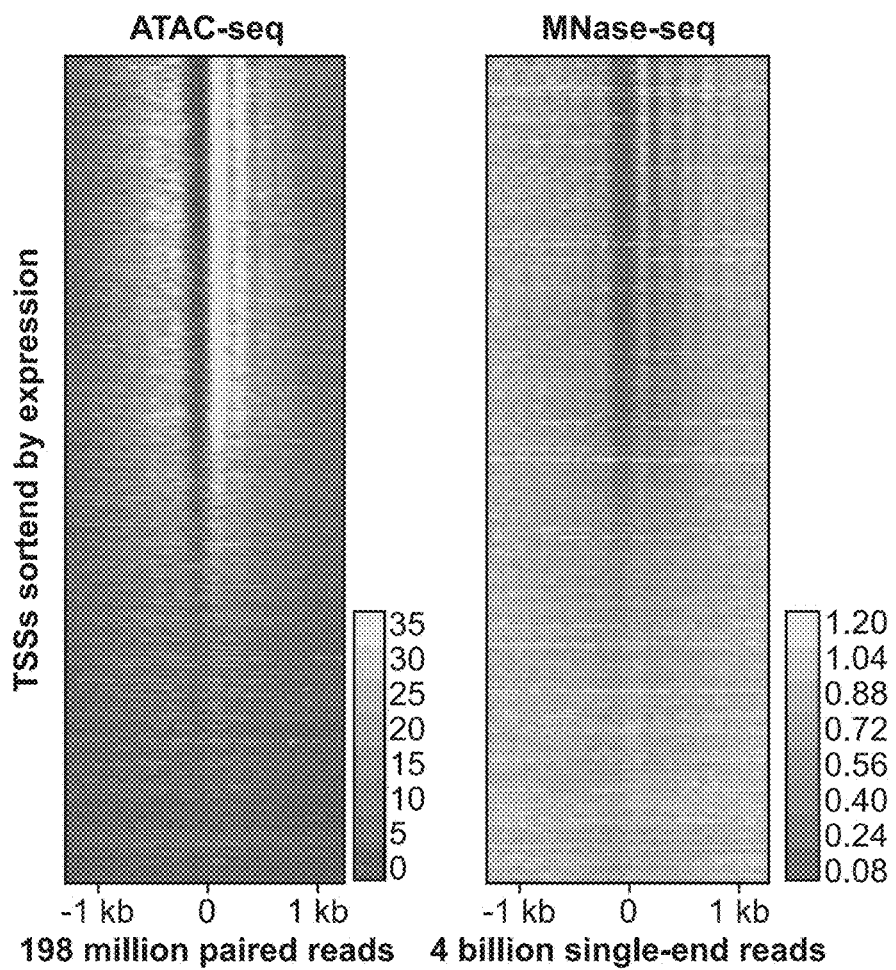
Figure 3C:
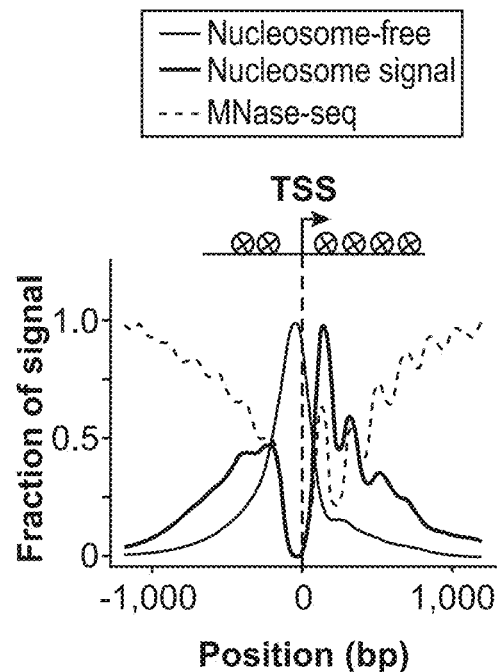

Nucleosome positioning: To generate the nucleosome position data track, we chose to split reads into various bins. Reads below 100 bps were considered nucleosome free, reads between 180 and 247 bps were considered to be mononucleosomes, reads between 315 and 473 bps were considered to be dinucleosomes and reads between 558 and 615 were considered to be trinucleosomes (for determining cutoffs see FIG. 12). Dinucleosome reads were split into two reads and Trinucleosome reads were split into three reads. Reads were analyzed using Danpos and Dantools using the parameters -p 1, -a 1, -d 20, -clonalcut 0. The background used was nucleosome free reads (reads less than 100 bps), allowing an effective negative weighting of these reads. This analysis allows calling multiple overlapping nucleosomes. Although generating nucleosome tracks using simple insert size cutoffs may yield false positives due to other nucleosome sized features, i.e. enhanaceosomes, we observed that we faithfully recapitulated global features on nucleosome position genome-wide (FIG. 3c,d main text).

ChIP-seq peak calling and clustering: ChIP-seq data was downloaded from the UCSC ENCODE repository. Peaks where called using GEM (Guo et al, *PLoS Comput. Biol.* 2012 8: e1002638), the parameters used where -k_min 6 -k_max 20. Inputs where used as a control for peak calling. Binding events were annotated by distance to the nearest dyad in bins of 10 bps. Factors were then hierarchically clustered using Euclidean distance and normalized by gene and centered by mean. (Eisen et al. *Proc. Natl. Acad. Sci.* 1998 95: 14863-14868).

Footprinting using CENTIPEDE: The genome-wide set of motifs were obtained from the ENCODE motif repository (at the website of broadinstitute.org). The input for CENTIPEDE included the PWM score, conservation (PhyloP) and ATAC-seq counts within +/−100bp of each genomic region matching a motif. ChIP-seq data was obtained from the UCSC ENCODE repository.

Comparison of transcription factor regulatory networks: Transcription factor regulatory networks were constructed by comparing the GENCODE v14 genes with the genome-wide set of posterior probabilities estimated by CENTIPEDE for the respective cell-types. The extent of a transcription factor regulating each gene was determined by taking the sum of the weighed posterior probabilities for a given transcription factor mapping to the same chromosome. For each mapped motif the posterior probability was weighted based on the distance to the transcription start site for each gene. Comparison of transcription factor regulatory networks was computed as the correlation of each transcription factor in a given cell type with all transcription factors in the other cell type. The resulting correlation matrix was hierarchically clustered using the Pearson correlation coefficient and complete linkage.

Candidate IL2 enhancer analysis: ENCODE data on the UCSC genome browser was inspected to identify putative IL2 enhancers in one or more cell types that may be responsive to FDA approved immomodulatory drugs. We scanned the intergenic region upstream of IL2 in hg19 for (i) enhancer-associated histone marks (H3K4me1 and H3K27ac), (ii) binding by one or more TFs as confirmed by ChIP-seq, and (iii) the TF pathway can be targeted by a human therapeutic. This analysis identified IRF4 and STAT5 binding sites in addition to the known NFAT-responsive elements.

Results

ATAC-Seq Probes Chromatin Accessibility with Transposons

Figure 1B:
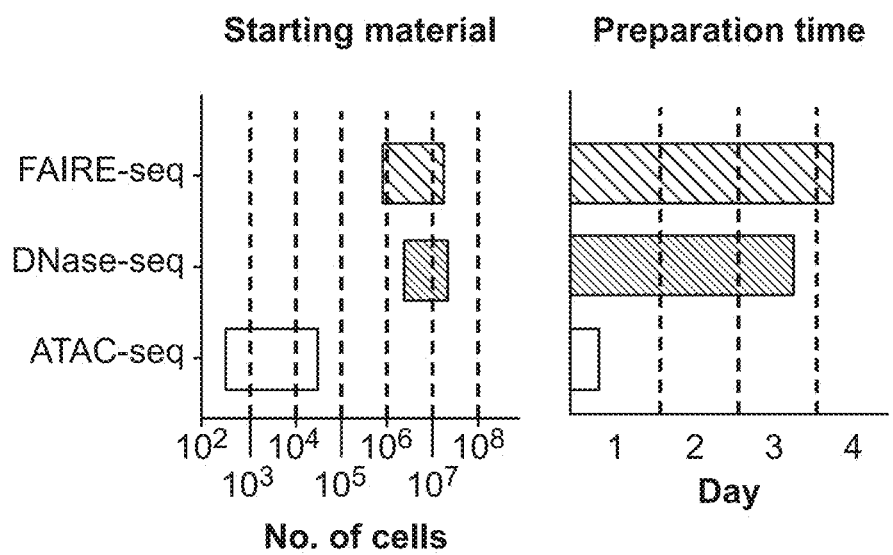

Hyperactive Tn5 transposase (Goryshin, J Biol Chem. 1998 273: 7367-7374; Adey, A. et al. *Genome Biol* 2010 11: R119, loaded in vitro with adapters for high-throughput DNA sequencing, can simultaneously fragment and tag a genome with sequencing adapters (previously described as "tagmentation"). It was hypothesized that transposition by purified Tn5, a prokaryotic transposase, on small numbers of unfixed eukaryotic nuclei would interrogate regions of accessible chromatin. An Assay for Transposase Accessible Chromatin followed by high-throughput sequencing (ATAC-seq) is described. ATAC-seq uses Tn5 transposase to integrate its adapter payload into regions of accessible chromatin, whereas steric hindrance less accessible chromatin makes transposition less probable. Therefore, amplifiable DNA fragments suitable for high-throughput sequencing are preferentially generated at locations of open chromatin (FIG. 1*a*). The entire assay and library construction can be carried out in a simple two-step process involving Tn5 insertion and PCR. In contrast, published DNase- and FAIRE-seq protocols for assaying chromatin accessibility involve multi-step protocols and many potentially loss-prone steps, such as adapter ligation, gel purification, and crosslink reversal. For instance, a published DNase-seq protocol calls for approximately 44 steps, and two overnight incubations, while published FAIRE-seq protocols require two overnight incubations carried out over at least 3 days. Furthermore, these protocols require 1-50 million cells (FAIRE) or 50 million cells (DNase-seq), perhaps because of these complex workflows (FIG. 1*b*). In comparison to established methods, ATAC-seq enables rapid and efficient library generation because assay and library preparation are carried out in a single enzymatic step.

Figure 1C:
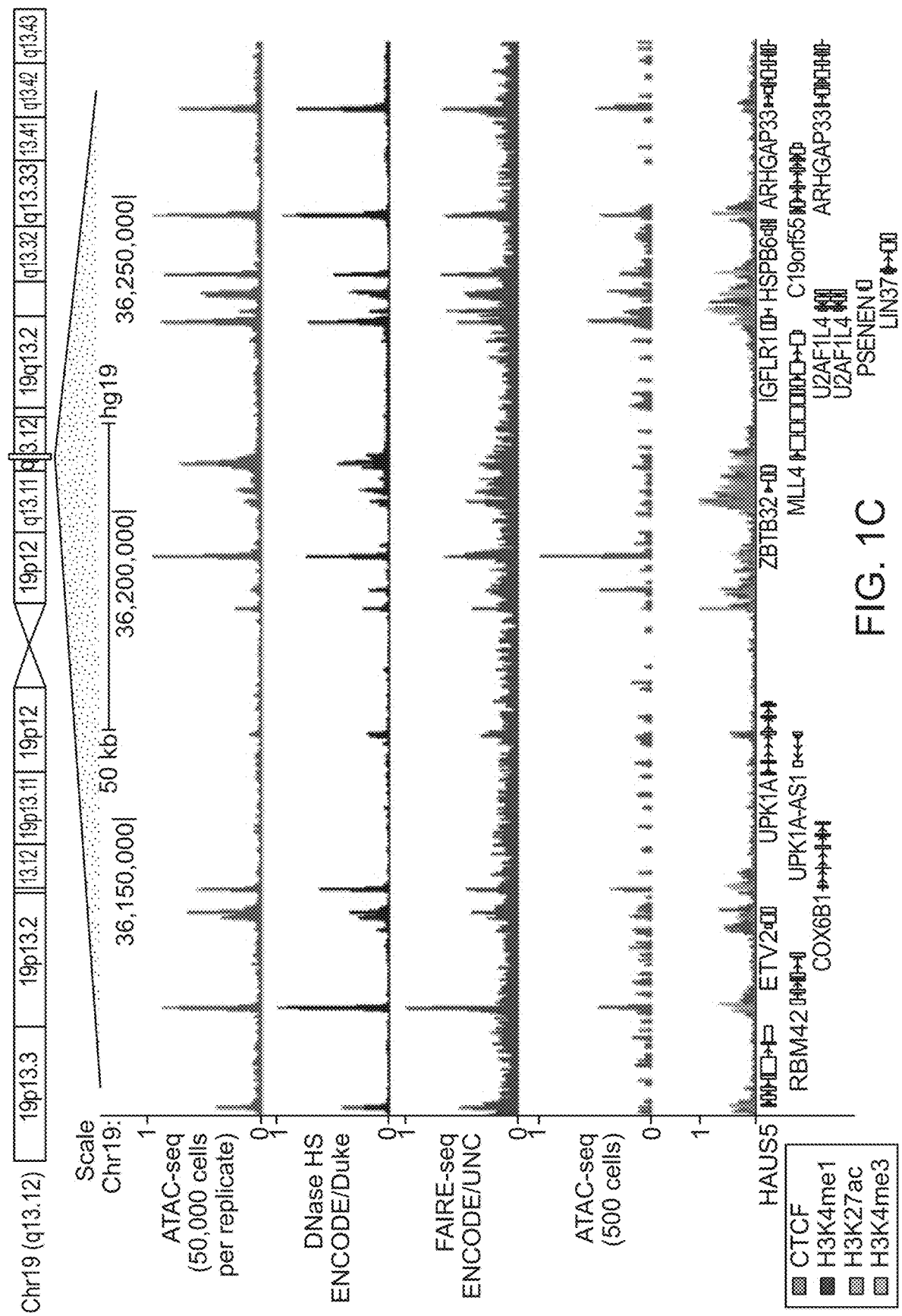
Figure 6:
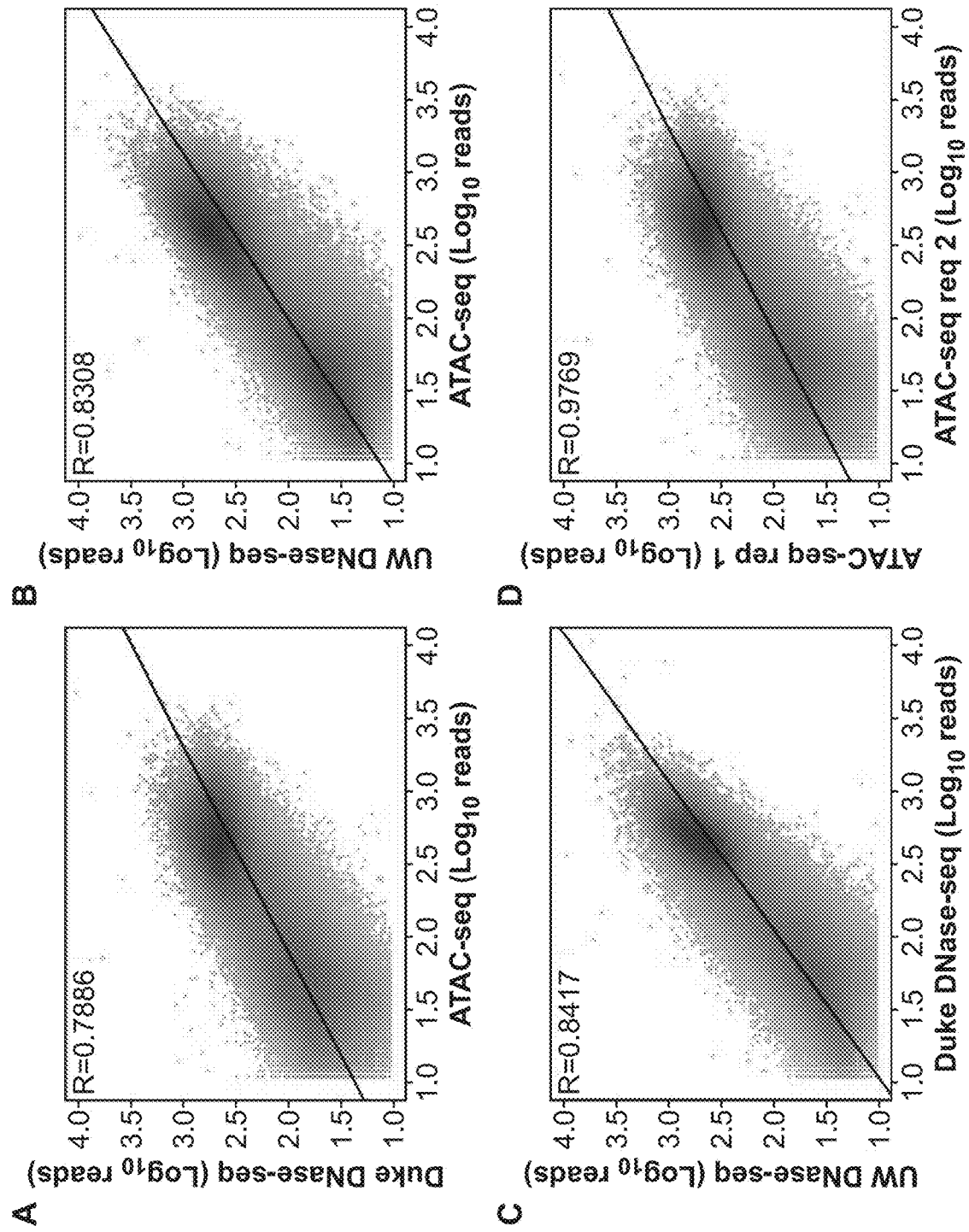
FIG. 6: ATAC-seq peak intensity correlates well with DNase-seq peak intensity. Peaks in Duke DNase-seq (down sampled to $60 \times 10^6$ reads), UW DNase-seq ($40 \times 10^6$ reads), and ATAC-seq data ($60 \times 10^6$ paired-end reads) were called using ZINBA (Rashid et al Genome Biol. 2011 12: R67). Because each data set has different read lengths we chose to filter for peaks within mappable regions (Duke DNase-seq=20 bp reads, UW DNase-Seq=36 bp reads and ATAC-Seq=paired-end 50 bp reads). The log 10(read intensity) was compared for (A) Duke DNase-seq and ATAC-seq, (B) UW DNase-seq and ATAC-seq, and (C) UW DNAse-seq and Duke DNase-seq. Technical reproducibility of ATAC-seq data is shown in D.
Figure 7:
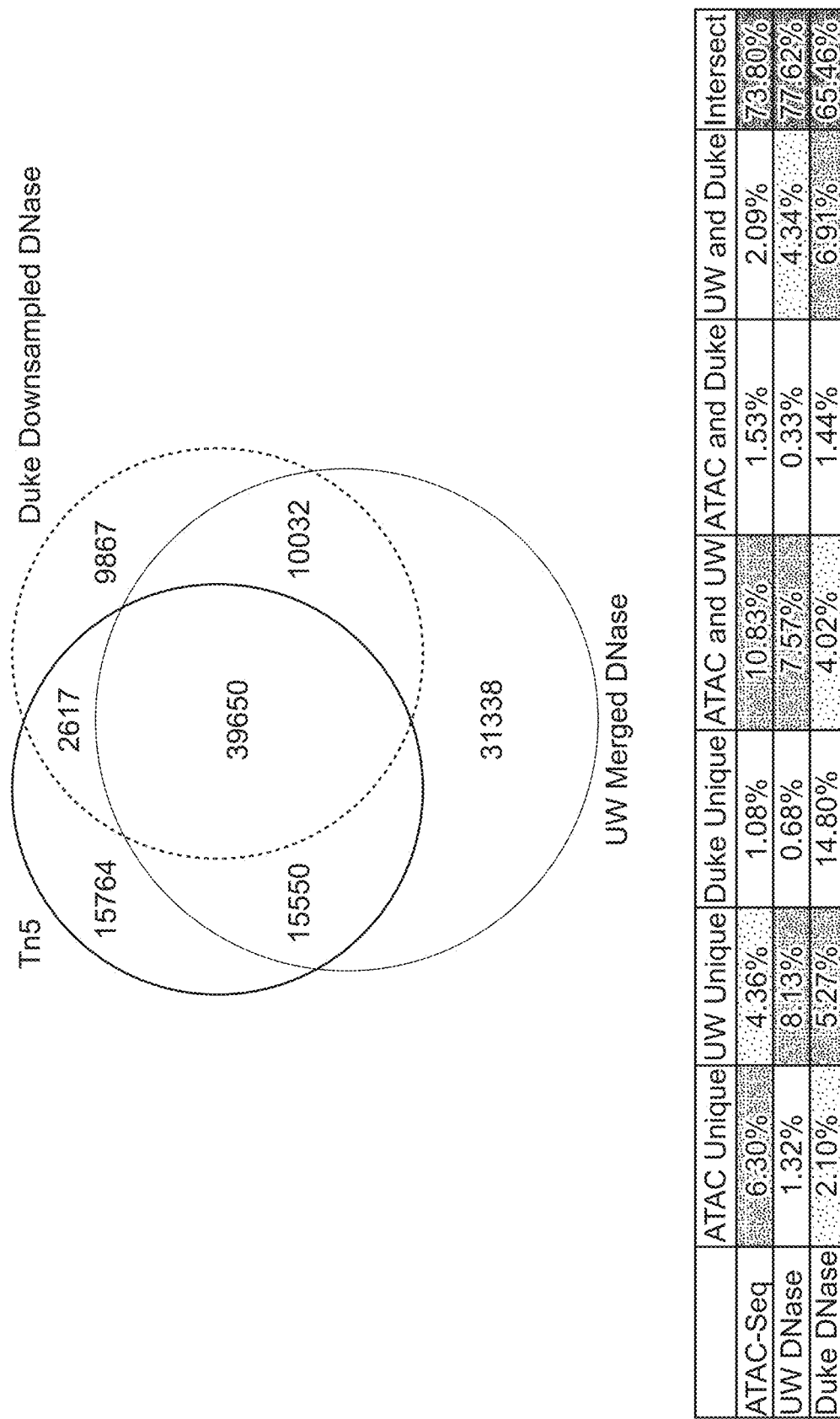
FIG. 7: ATAC-seq captures a large fraction of DNase identified peaks. Peaks were called for all data sets using ZINBA. The venn-diagram shows overlap of the peak calls between each method. Below: The majority of ATAC-seq reads are in intense peaks that intersect with Duke and UW DNase-seq peaks. The total fraction of reads within peaks called from ATAC-seq, UW DNase-seq, and Duke DNase-seq, as well as the intersections of these data are shown. More than 65% of reads from all three methods are found in the intersection of the three methods' peaks, suggesting that strong well-stereotyped peaks are detected by all methods. Table cell color is proportional to fraction of reads.
Figure 8:
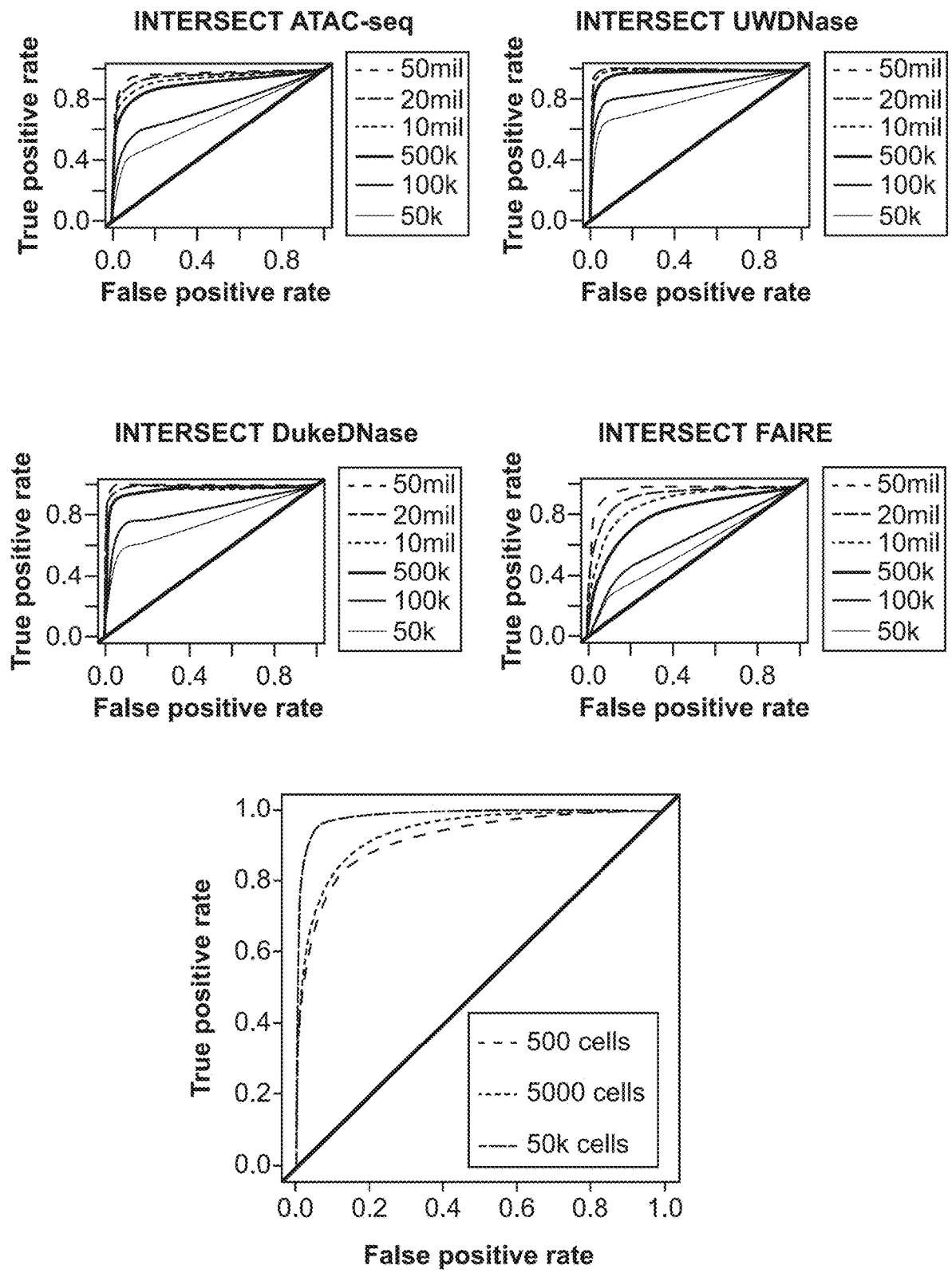
FIG. 8: Graphs of the number of reads overlapping the set of open chromatin regions identified by Duke DNase, UW DNase and FAIRE in GM12878 cells compared to a set of background regions, wherein to determine the read depth required for detecting open chromatin sites sensitivity and specificity was assessed at varying read depths, including 50 k, 100 k, 500 k, 10 million and 50 million reads. The bottom graph shows the performance of ATAC-seq in GM12878 cells was assessed using 500, 5,000 or 50,000 cells as starting material.
Figure 9:
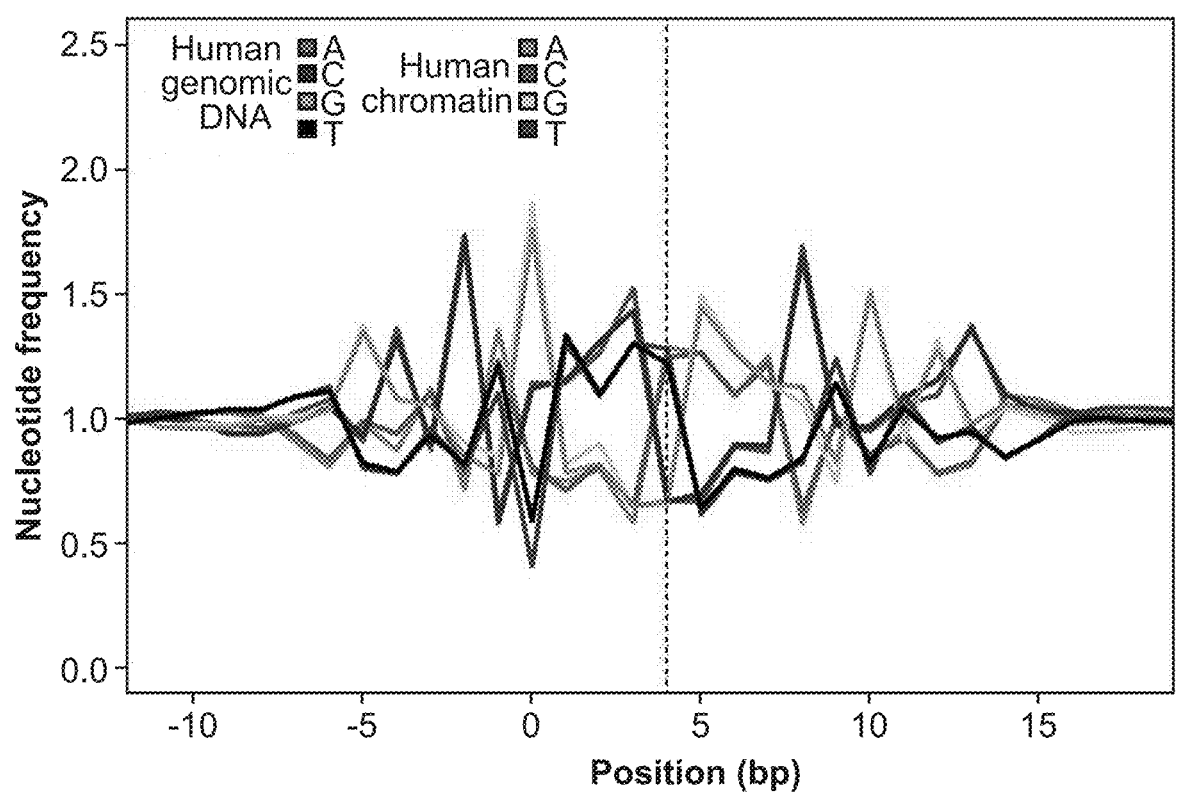
FIG. 9: Tn5 insertion preferences in genomic DNA and chromatin. Nucleotide frequency scores represent the observed nucleotide frequency of each base, nucleotide frequencies are normalized to 1. The x=0 position represents the read start, and the dotted line represents the symmetry axis of the Tn5 dimer. We see no substantial differences between Tn5 insertion preferences between purified genomic DNA and human chromatin, suggesting that the local insertion preference into chromatin is identical to that found in naked genomic DNA. These reported sequence preferences are similar to those previously reported (main text ref. 11).
Figure 10:
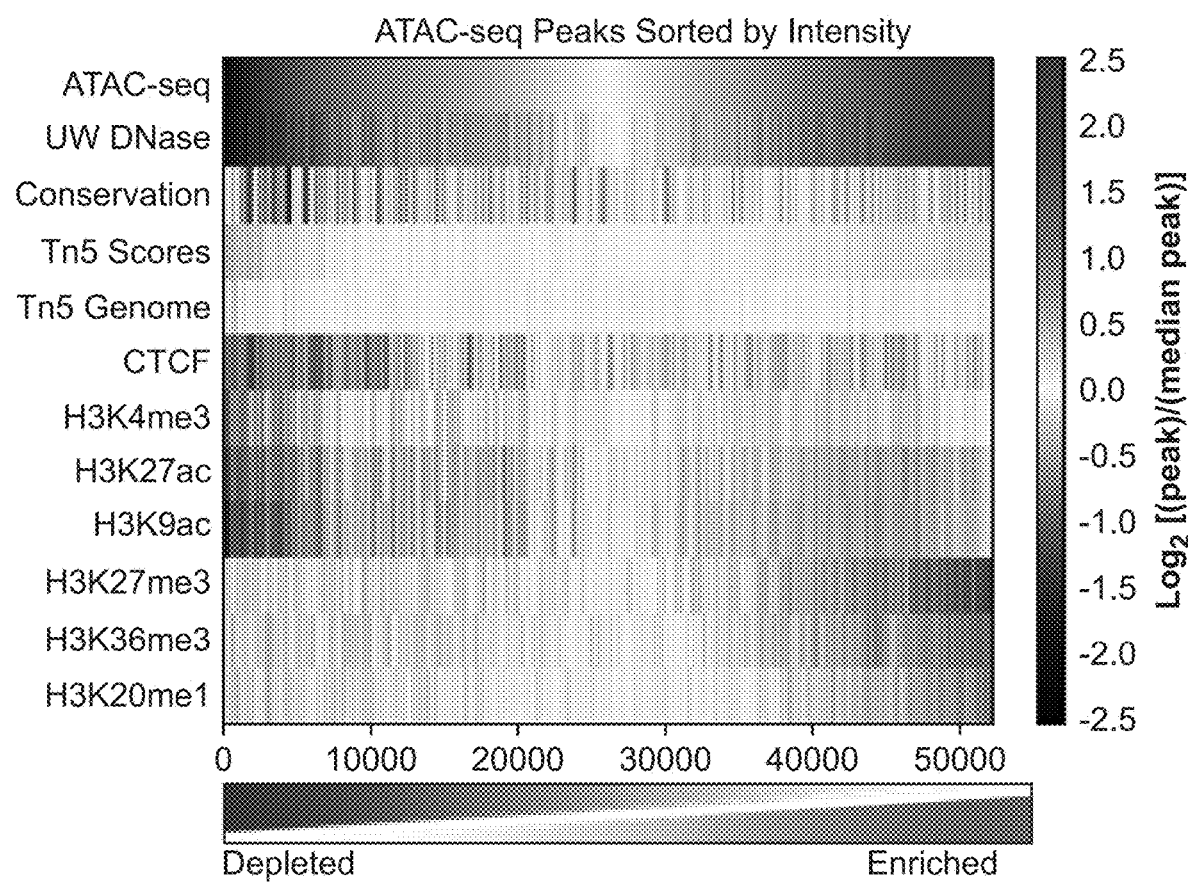
FIG. 10: Graph of the average intensity per base of each feature at every ATAC-seq peak; all ENCODE ChIP data was normalized to input; data has been processed using a sliding window of 200 peaks.
Figure 11:
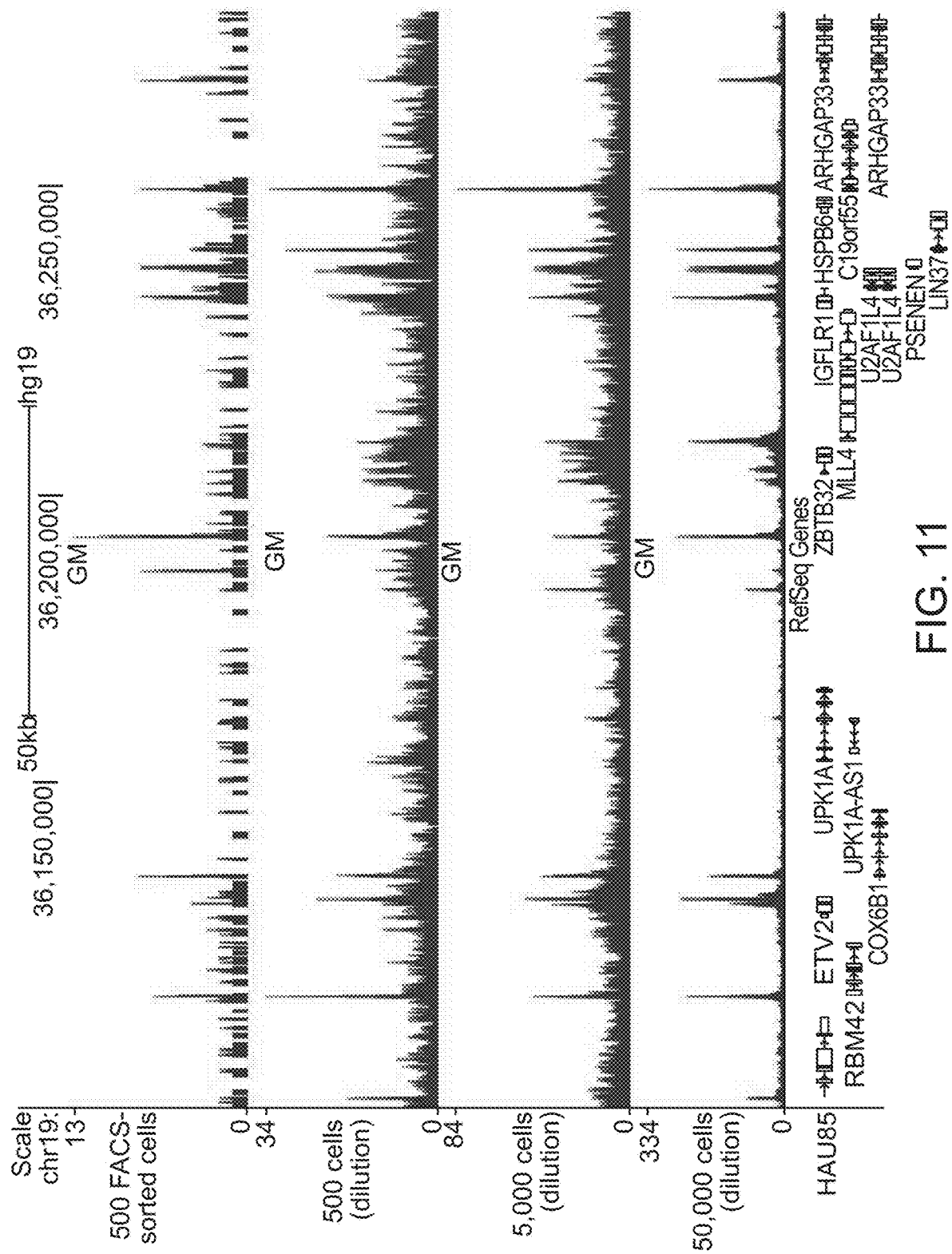
FIG. 11: ATAC-seq of various cell numbers. A representative UCSC genome browser track of data from different starting numbers of cells for ATAC-seq. This same locus is also shown in FIG. 1b of the main text. In order: 500 cells were isolated using FACS and two replicates of 500 cells and 5,000 cells were done by a simple dilution from cell culture. For comparison, the bottom track represents 50,000 cells, also show in FIG. 1b. This figure demonstrates that we are able to capture open chromatin sites from as few as 500 cells.

Extensive analyses show that ATAC-seq provides accurate and sensitive measure of chromatin accessibility genome-wide. ATAC-seq was carried out on 50,000 and 500 unfixed nuclei isolated from GM12878 lymphoblastoid cell line (ENCODE Tier 1) for comparison and validation with chromatin accessibility data sets, including DNase-seq and FAIRE-seq. At a locus previously highlighted by others, (FIG. 1*c*), ATAC-seq has a signal-to-noise ratio similar to DNase-seq, which was generated from approximately 3 to 5 orders-of-magnitude more cells. Peak intensities were highly reproducible between technical replicates (R=0.98), and highly correlated between ATAC-seq and DNase-seq (R=0.79 and R=0.83, FIG. 6), and it is noted that the majority of reads within peaks come from intersections of DNase and ATAC-seq peaks (FIG. 7). Comparing our data to DHSs identified in ENCODE DNase-seq data, receiver operating characteristic (ROC) curves demonstrate a similar sensitivity and specificity as DNase-seq (FIG. 8). It is also noted that ATAC-seq peak intensities correlate well with markers of active chromatin and not with transposase sequence preference (FIGS. 9 and 10). Highly sensitive open chromatin detection is maintained even when using 5,000 or 500 human nuclei as starting material (FIGS. 8 and 11), although, under the conditions used, sensitivity is diminished for smaller numbers of input material, as can be seen in FIG. 1*c*.

ATAC-Seq Insert Sizes Disclose Nucleosome Positions

Figure 2A:
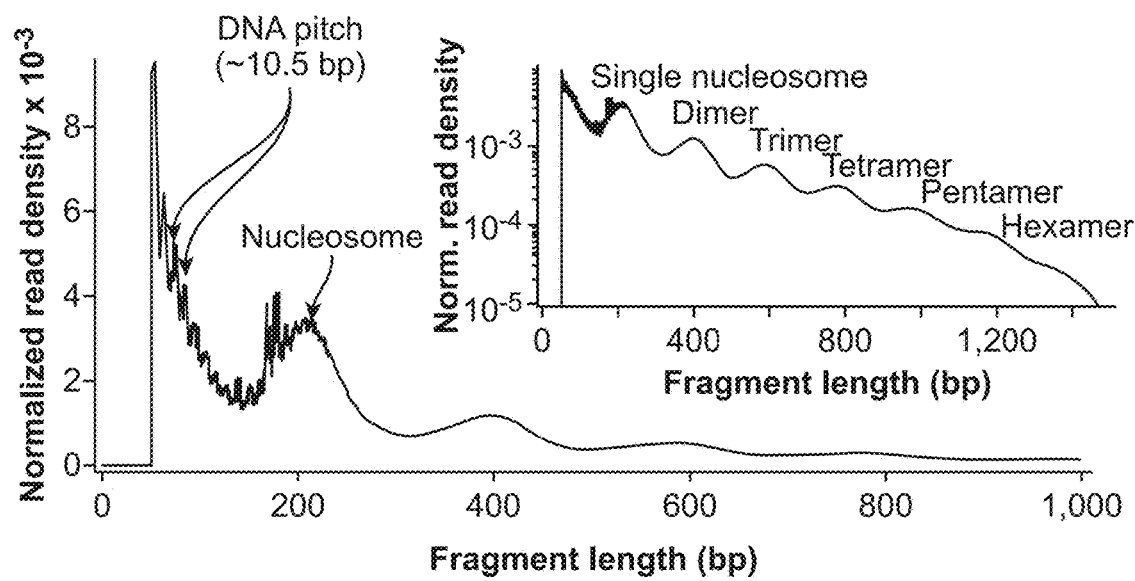
FIGS. 2A-2B: ATAC-seq provides genome-wide information on chromatin compaction. (a) ATAC-seq fragment sizes generated from GM12878 nuclei (red) indicate chromatin-dependent periodicity with a spatial frequency consistent with nucleosomes, as well as a high frequency periodicity consistent with the pitch of the DNA helix for fragments less than 200 bp. (Inset) log-transformed histogram shows clear periodicity persists to 6 nucleosomes. (b) Normalized read enrichments for 7 classes of chromatin state previously defined.
Figure 2B:
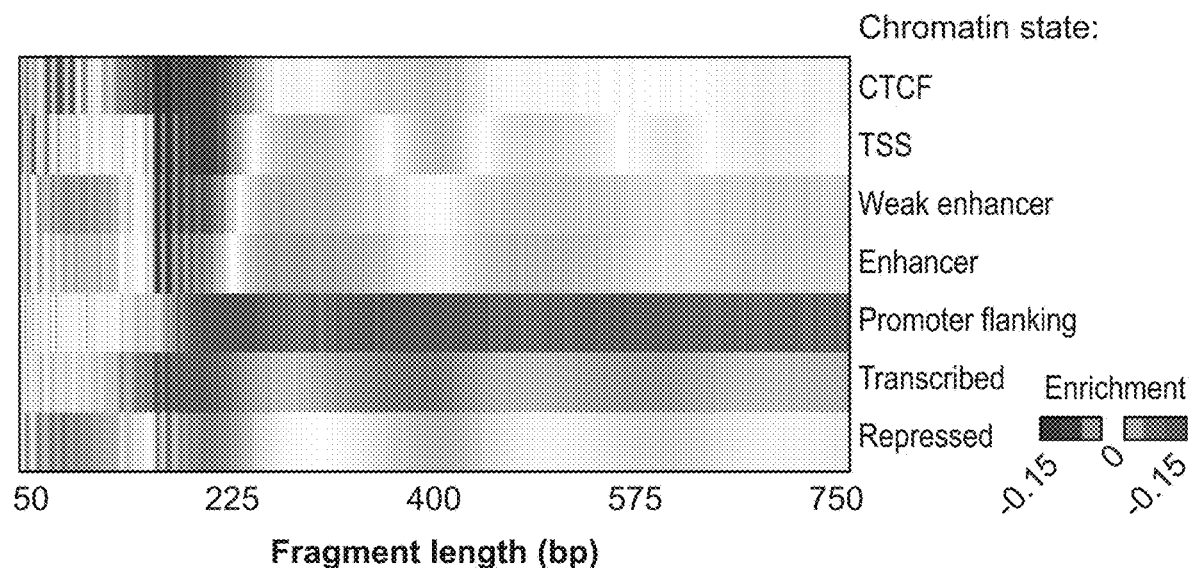

It was found that ATAC-seq paired-end reads produce detailed information about nucleosome packing and positioning. The insert size distribution of sequenced fragments from human chromatin has clear periodicity of approximately 200 base pairs, suggesting many fragments are protected by integer multiples of nucleosomes (FIG. 2*a*). This fragment size distribution also shows clear periodicity equal to the helical pitch of DNA. By partitioning insert size distribution according to functional classes of chromatin as defined by previous models (Hoffman et al. Nucleic Acids Res. 2013 41: 827-841), and normalizing to the global insert distribution we observe clear class-specific enrichments across this insert size distribution (FIG. 2*b*), demonstrating that these functional states of chromatin have an accessibility "fingerprint" that can be read out with ATAC-seq. These differential fragmentation patterns are consistent with the putative functional state of these classes, as CTCF-bound regions are enriched for short fragments of DNA, while transcription start sites are differentially depleted for mono-, di- and tri-nucleosome associated fragments. Transcribed and promoter flanking regions are enriched for longer multi-nucleosomal fragments, suggesting they may represent more compacted forms of chromatin. Finally, prior studies have shown that certain DNA sequences are refractory to nuclease digestion and released as large, multi-nucleosome-sized fragments; subsequent studies showed that such fragments are condensed heterochromatin. Indeed repressed regions were found to be depleted for short fragments and enriched for phased multi-nucleosomal inserts, consistent with their expected inaccessible state. These data suggest that ATAC-seq reveals differentially accessible forms of chromatin, which have been long hypothesized to exist in vivo.

Figure 3D:
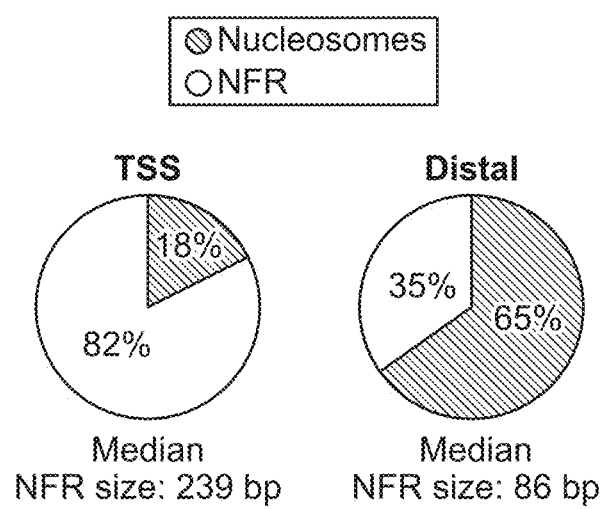
Figure 12:
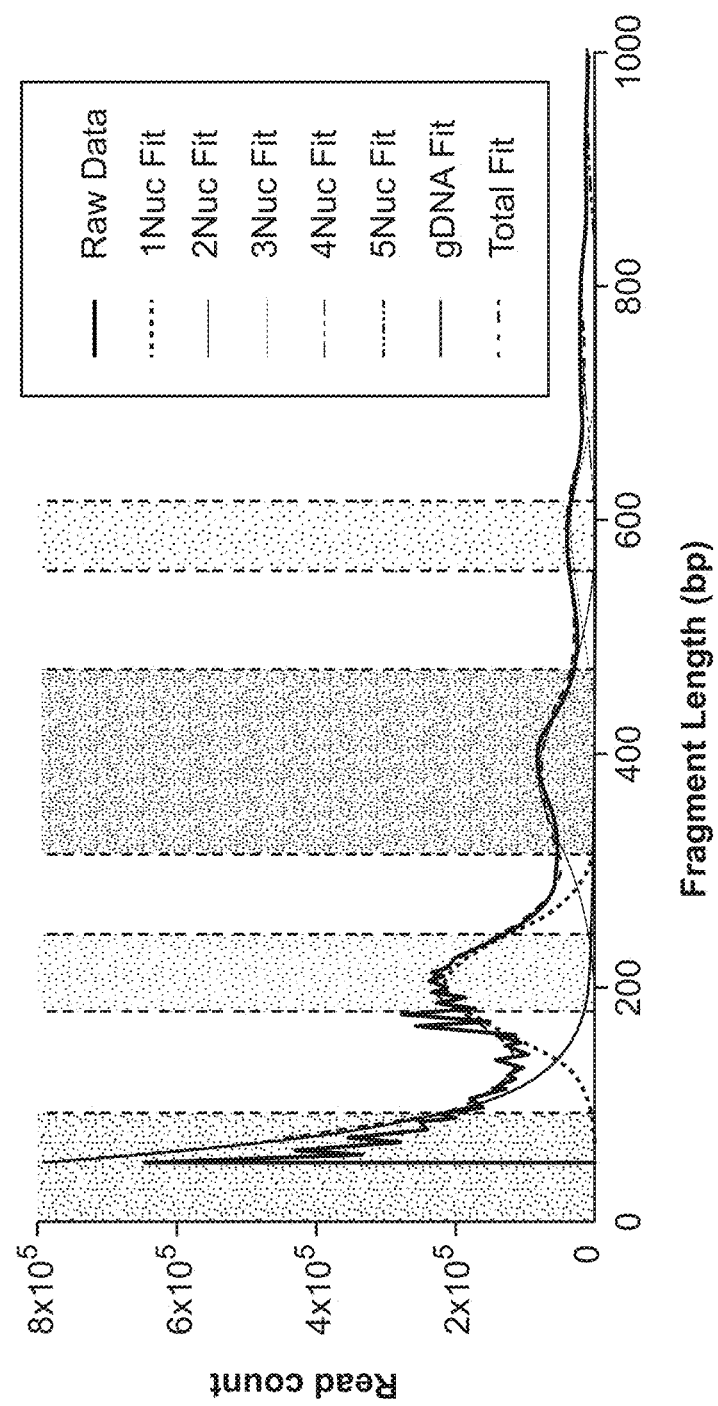
FIG. 12: Fitting nucleosome peaks in ATAC-seq fragment size distribution to enable nucleosome occupancy measurements. The observed fragment distribution was partitioned into four populations of reads—reads expected to originate from open DNA, and reads that span 1, 2 or 3 putative nucleosomes. To enable this partitioning of the data, the ATAC-seq fragment distribution was fit to the sum of 1) an exponential function for fragment distribution pattern at insert sizes below one nucleosome, and 2) 5 Gaussians to the distributions arising from protection from one, two, three, four and five nucleosomes. The sum of these fits is shown (black dotted line) is similar to the observed fragment distribution (blue line). Vertical dotted lines are boundaries for identification of fragments as originating from the nucleosome-free (<100 bps), 1-nucleosome, 2-nucleosome and 3-nucleosome regions. Dotted lines were set to ensure that <10% of fragments originate from neighboring, as defined by our fit.

To explore nucleosome positioning within accessible chromatin in the GM12878 cell line, data was partitioned into reads generated from putative nucleosome free regions of DNA, and reads likely derived from nucleosome associated DNA (see FIG. 12). Using a simple heuristic that positively weights nucleosome associated fragments and negatively weights nucleosome free fragments (see Methods), we calculated a data track used to call nucleosome positions within regions of accessible chromatin (Chen, K. et al. Genome Research 2013 23, 341-351). An example locus (FIG. 3a) contains a putative bidirectional promoter with CAGE data showing two transcription start sites (TSS) separated by ~700 bps. ATAC-seq reveals in fact two distinct nucleosome free regions, separated by a single well-positioned mononucleosome (FIG. 3a). Compared to MNase-seq, ATAC-seq data is more amenable to detecting nucleosomes within putative regulatory regions, as the majority of reads are concentrated within accessible regions of chromatin (FIG. 3b). By averaging signal across all active TSSs, it is noted that nucleosome-free fragments are enriched at a canonical nucleosome-free promoter region overlapping the TSS, while the nucleosome signal is enriched both upstream and downstream of the active TSS, and displays characteristic phasing of upstream and downstream nucleosomes (FIG. 3c). Because ATAC-seq reads are concentrated at regions of open chromatin, a strong nucleosome signal is seen at the +1 nucleosome, which decreases at the +2, +3 and +4 nucleosomes, in contrast, MNase-seq nucleosome signal increases at larger distances from the TSS likely due to over digestion of more accessible nucleosomes. Additionally, MNase-seq (4 billion reads) assays all nucleosomes, whereas reads generated from ATAC-seq (198 million paired reads) are concentrated at regulatory nucleosomes (FIG. 3b,c). Using the nucleosome calls, putative distal regulatory regions and TSSs were further partititioned into regions that were nucleosome free and regions that were predicted to be nucleosome bound. It is noted that TSSs were enriched for nucleosome free regions when compared to distal elements, which tend to remain nucleosome rich (FIG. 3d). These data suggest ATAC-seq can provide high-resolution readout of nucleosome associated and nucleosome free regions in regulatory elements genome wide.

ATAC-Seq Reveals Patterns of Nucleosome-TF Spacing

Figure 3E:
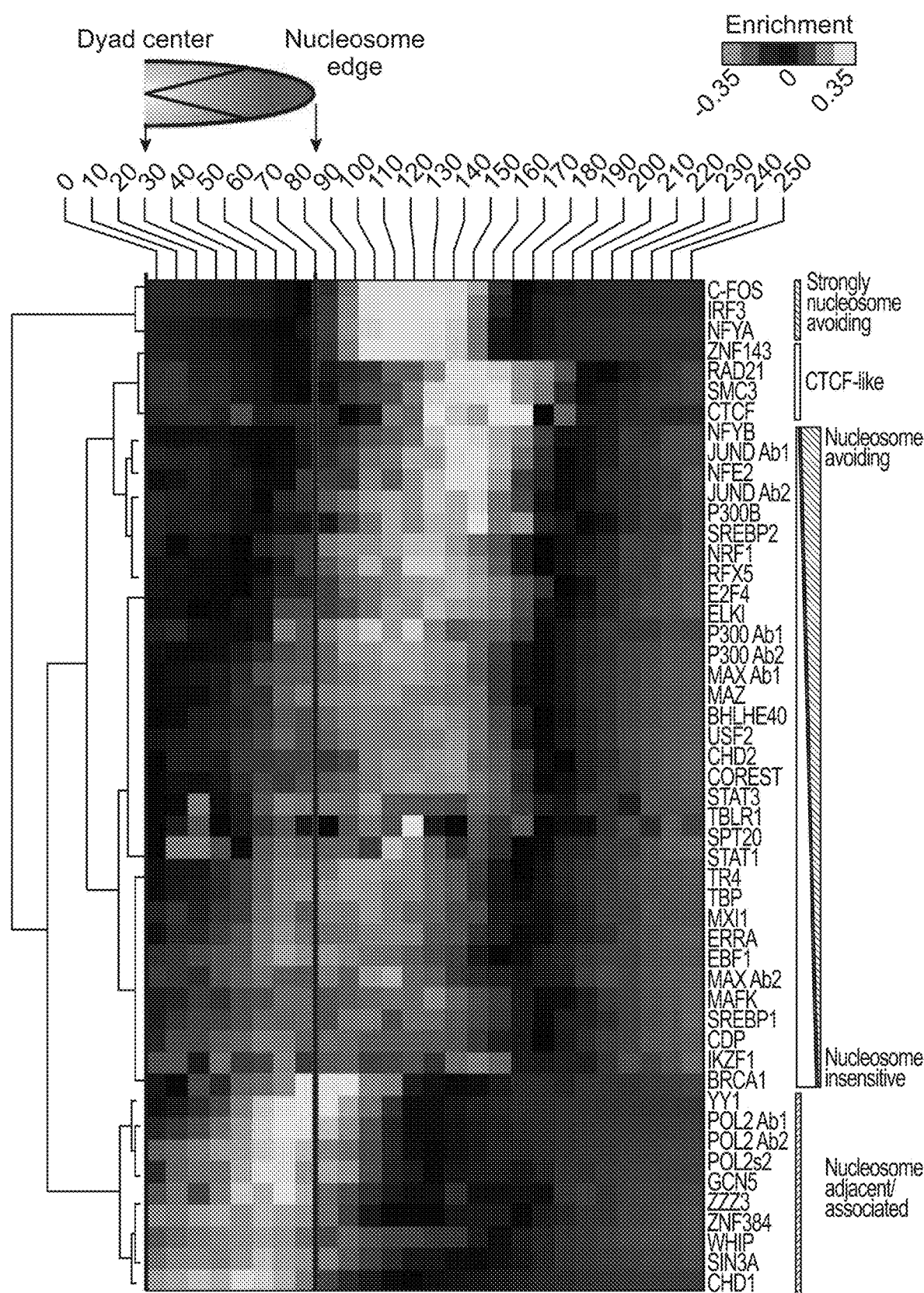

ATAC-seq high-resolution regulatory nucleosome maps can be used to understand the relationship between nucleosomes and DNA binding factors. Using ChIP-seq data, we plotted the position of a variety of DNA binding factors with respect to the dyad of the nearest nucleosome. Unsupervised hierarchical clustering (FIG. 3e) revealed major classes of binding with respect to the proximal nucleosome, including 1) a strongly nucleosome avoiding group of factors with binding events stereotyped at ~180 bases from the nearest nucleosome dyad (comprising C-FOS, NFYA and IRF3), 2) a class of factors that "nestle up" precisely to the expected end of nucleosome DNA contacts, which notably includes chromatin looping factors CTCF and cohesion complex subunits RAD21 and SMC3; 3) a large class of primarily TFs that have gradations of nucleosome avoiding or nucleosome-overlapping binding behavior, and 4) a class whose binding sites tend to overlap nucleosome-associated DNA. Interestingly, this final class includes chromatin remodeling factors such as CHD1 and SIN3A as well as RNA polymerase II, which appears to be enriched at the nucleosome boundary. The interplay between precise nucleosome positioning and locations of DNA binding factor immediately suggests specific hypotheses for mechanistic studies, a potential advantage of ATAC-seq.

ATAC-Seq Footprints Infer Factor Occupancy Genome-Wide

Figure 13:
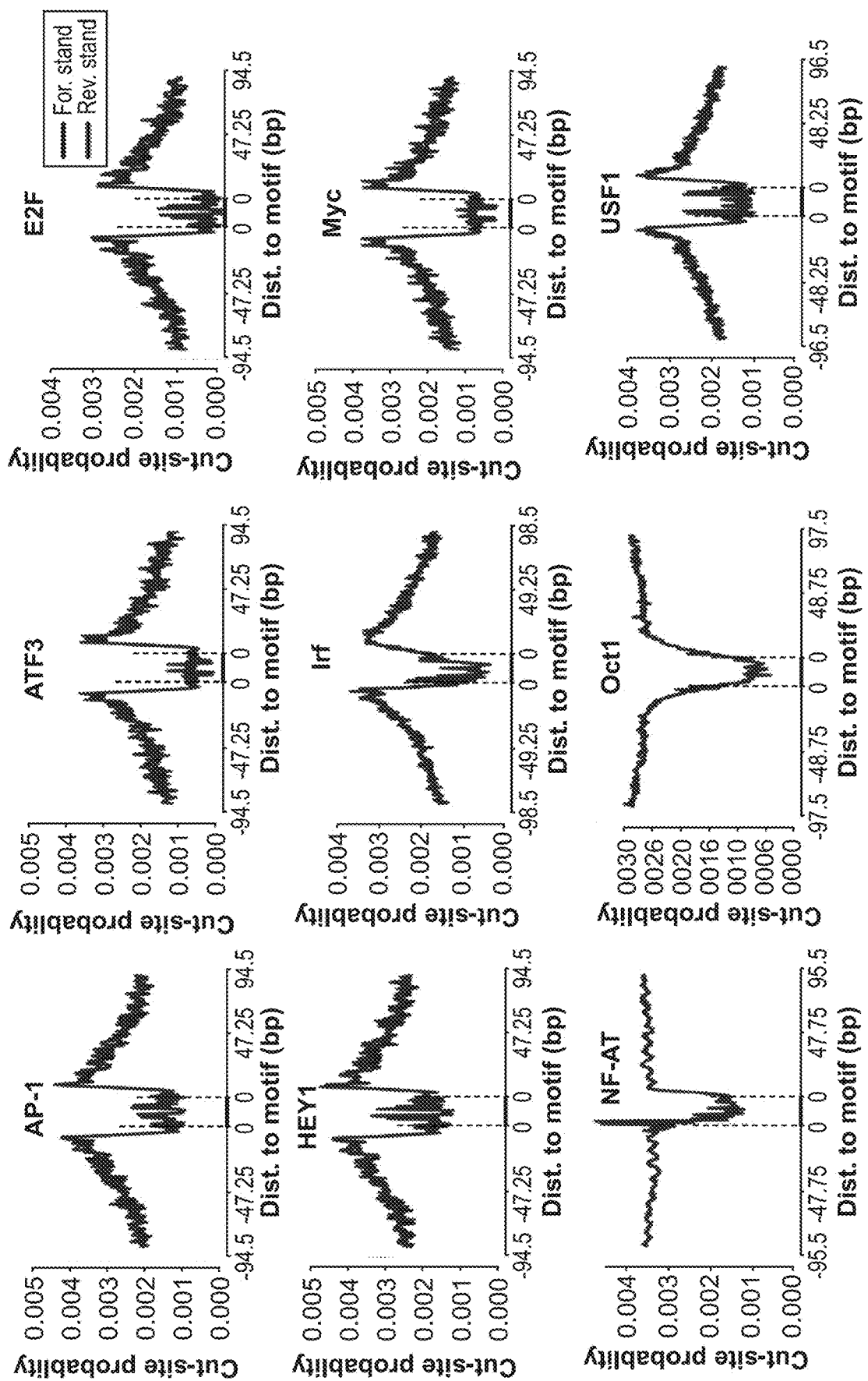
FIG. 13: Select set of transcription factor footprints detected by ATAC-seq in GM12878 cells. For the indicated transcription factors the aggregate signal of ATAC-seq reads were computed using CENTIPEDE on the genome-wide sets of sites matching the corresponding motif. Reads were calculated in the region +/−100 bp of the motif boundary. The vertical dashed lines indicate the boundaries of the motifs.
Figure 14:
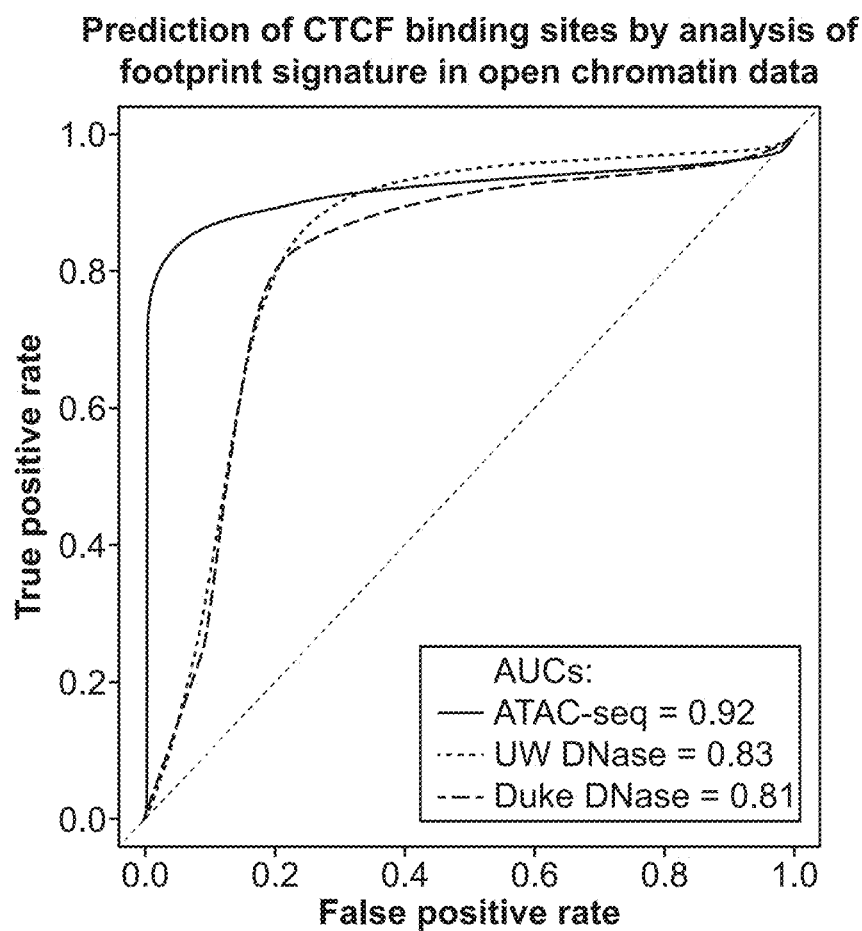
FIG. 14: Prediction of CTCF binding sites using ATAC-seq and DNase footprinting with CENTIPEDE. Prediction of CTCF binding sites was assessed using the genome-wide set of CTCF motifs sorted by the posterior probability reported by CENTIPEDE. Those overlapping CTCF ChIP-seq peaks were used as the positive set and all others were considered as the negative set. This yielded an area under the curve (AUC) of 0.92, which suggests specific and sensitive binding inference for CTCF. Duke DNase and UW DNase data were used with the same settings of CENTIPEDE, and ROC plots are shown. ATAC-seq data consisted of $198 \times 10^6$ paired reads, Duke DNase-comprised $245 \times 10^6$ reads, and UW DNase comprised $48 \times 10^6$ reads.

ATAC-seq enables accurate inference of DNA binding factor occupancy genome-wide. DNA sequences directly occupied by DNA-binding proteins should be protected from transposition; the resulting sequence "footprint" reveals the presence of the DNA-binding protein at each site, analogous to DNase digestion footprints. At a specific CTCF binding site on chromosome 1, we observed a clear footprint (a deep notch of ATAC-seq signal), similar to footprints seen by DNase-seq, at the precise location of the CTCF motif that coincides with the summit of the CTCF ChIP-seq signal in GM12878 cells (FIG. 4a). The ATAC-seq signal was averaged over all expected locations of CTCF within the genome and observed a well-stereotyped "footprint" (FIG. 4b). Similar results were obtained for a variety of common TFs (for examples see FIG. 13). We inferred the CTCF binding probability from motif consensus score, evolutionary conservation, and ATAC-seq insertion data to generate a posterior probability of CTCF binding at all loci (FIG. 4c) (Pique-Regi et al. Genome Research 2011 21 447-455). Results using ATAC-seq closely recapitulate ChIP-seq binding data in this cell line and compare favorably to DNase-based factor occupancy inference (see FIG. 14), suggesting that factor occupancy data can be extracted from these ATAC-seq data allowing reconstruction of regulatory networks.

ATAC-Seq Enables Epigenomic Analysis on Clinical Timescales

Figure 5A:
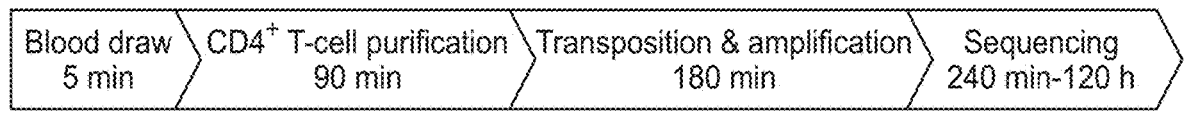
FIGS. 5A-5D: ATAC-seq enables real-time personal epigenomics. (a) Work flow from standard blood draws. (b) Serial ATAC-seq data from proband T-cells over three days. (c) Example of application of ATAC-seq data (green track) to prioritize candidate TF drug targets. Among identified TF binding sites proximal to cytokine gene IL2 that can be targeted by FDA-approved drugs, only NFAT is engaged in proband T-cells. ATAC-seq footprint prediction is confirmed by alignment with published NFAT ChIP-seq data (blue track, data from ref[35]). (d) Cell type-specific regulatory network from proband T cells compared with GM12878 B-cell line. Each row or column is the footprint profile of a TF versus that of all other TFs in the same cell type. Color indicates relative similarity (yellow) or distinctiveness (blue) in T versus B cells. NFAT is one of the most highly differentially regulated TFs (red box) whereas canonical CTCF binding is essentially similar in T and B cells.
Figure 5B:
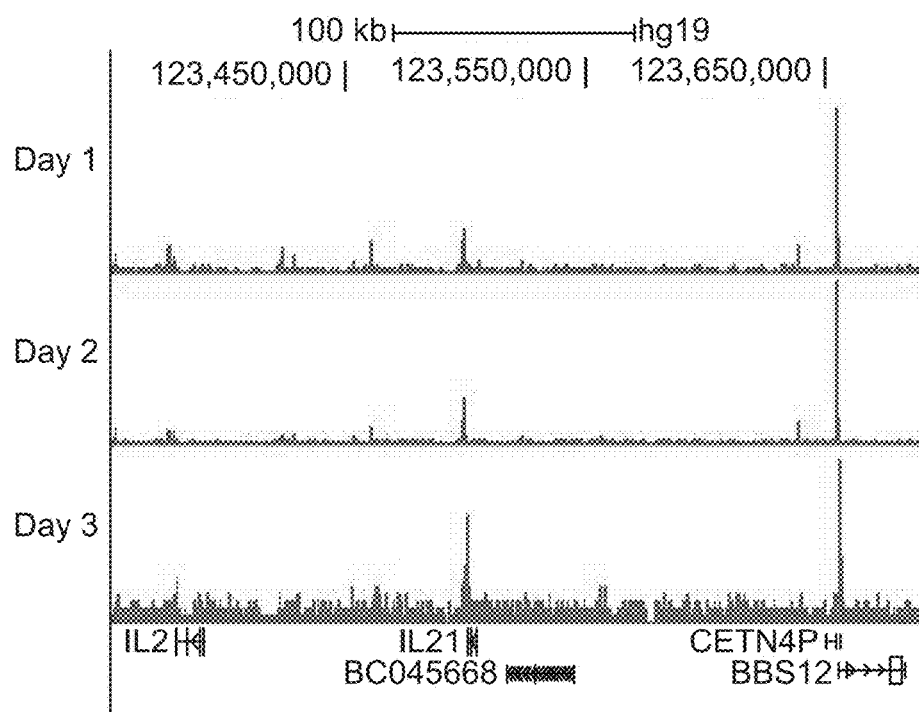
Figure 5C:
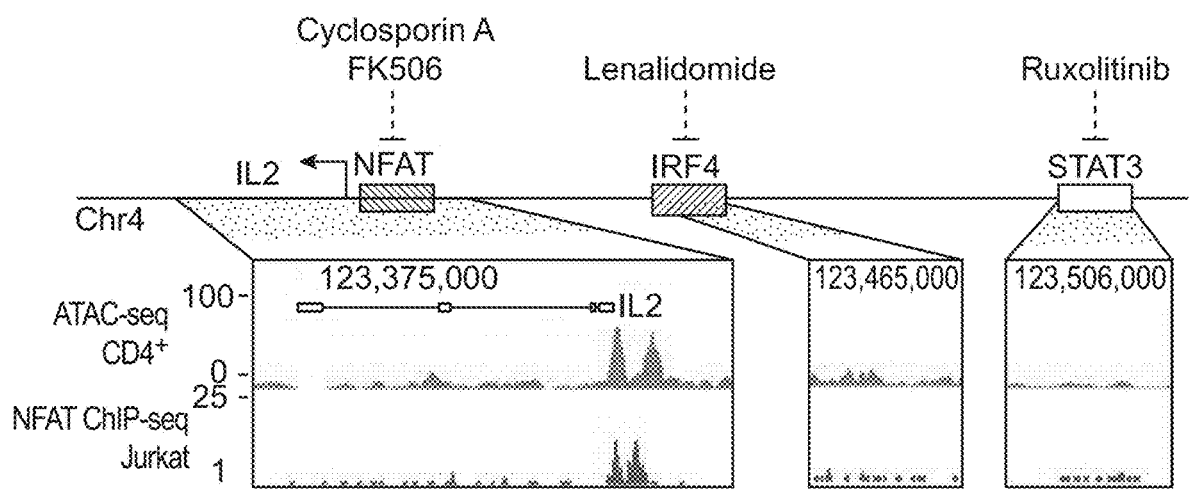

ATAC-seq is rapid, information rich, and compatible with small numbers of cells and may serve as a powerful tool for personalized epigenomics in the clinic. Specifically, one can envision "personal epigenomics" as genome-scale information about chromatin generated from an individual from a standard clinical sample in a clinical timescale. ATAC-seq was applsied to assay the personal T-cell epigenome of a healthy volunteer via standard serial blood draws, to demonstrate a workflow capable of generating ATAC-seq libraries in clinical timescales. Using rapid T-cell enrichment and sample handling protocols, the total required time from blood draw to sequencing was approximately 275 minutes (FIG. 5a). When coupled with ongoing improvements to sequencing and analysis turn-around times, ATAC-seq can offer the possibility of a daily turn-around time for a personal epigenomic map. To explore this possibility, ATAC-seq was performed on three consecutive days via standard blood draws from a single individual (FIG. 5b). As an exercise to consider how personal epigenomic maps may contain personalized regulatory information, we investigated ATAC-seq profile at the IL2 locus. IL-2 is a key cytokine that drives T-cell growth and functions in inflammatory and autoimmune diseases. Furthermore, distinct drugs inhibit the activities of different transcription factors that bind putative IL2 enhancers in a context-dependent manner. In principle, one might wish to identify the causal transcription factor pathway in order to rationally target inhibition without exposing the patient to drugs unlikely to serve the therapeutic goal of IL-2 blockade. ATAC-seq shows that in the proband's T-cells, only NFAT, but not two other drug targets, is engaging IL2 (FIG. 5c), providing clinically relevant information on the regulatory state of this individual.

Figure 5D:
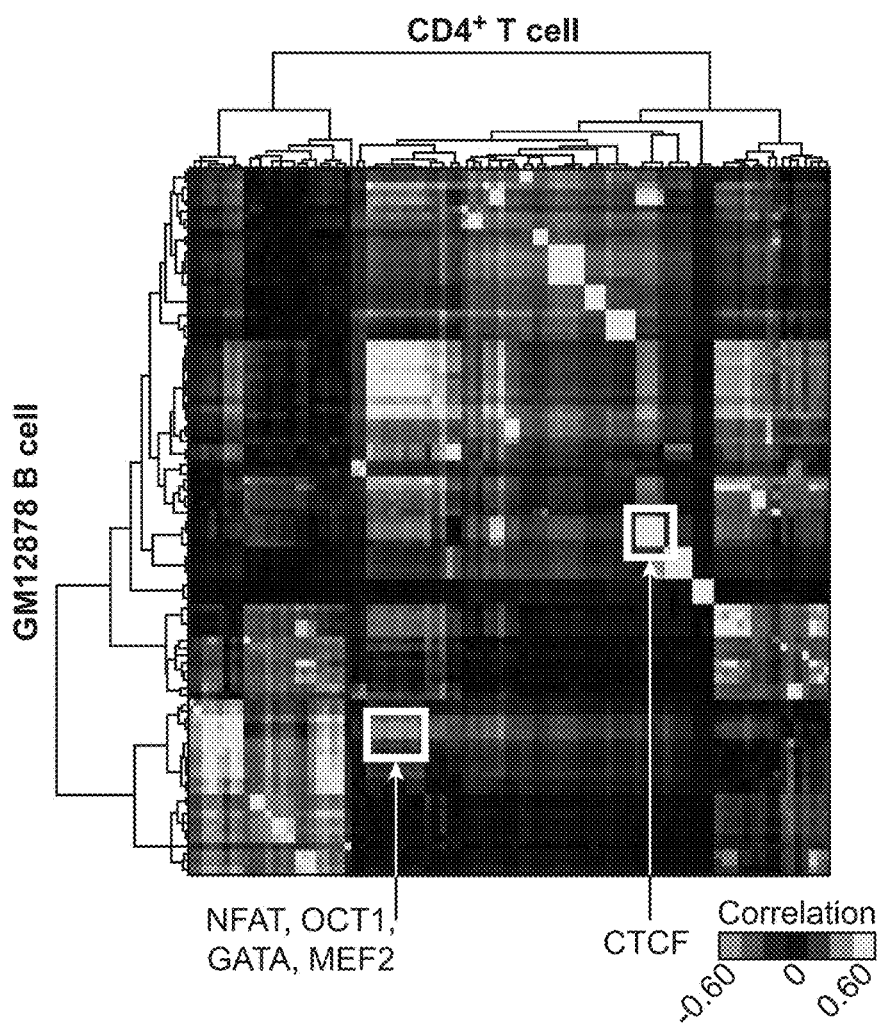
Figure 15:
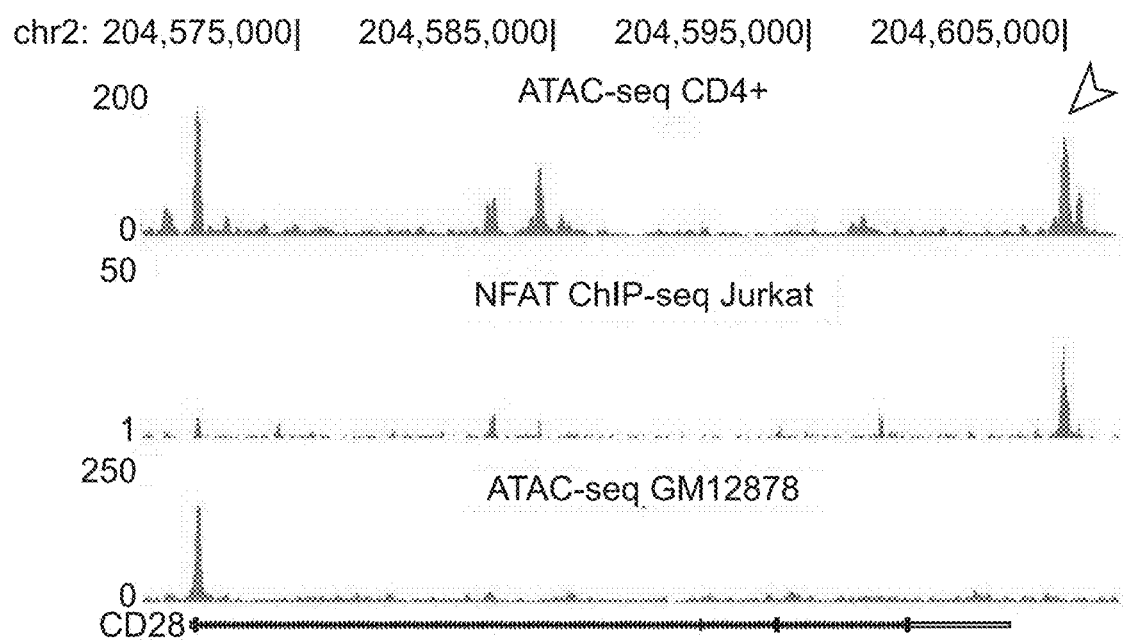
FIG. 15: T-cell specific NFAT regulation: Examples of T-cell-specific NFAT target genes predicted by ATAC-seq and confirmed by alignment with NFAT ChIP-seq (data from main text ref 35).
Figure 15:
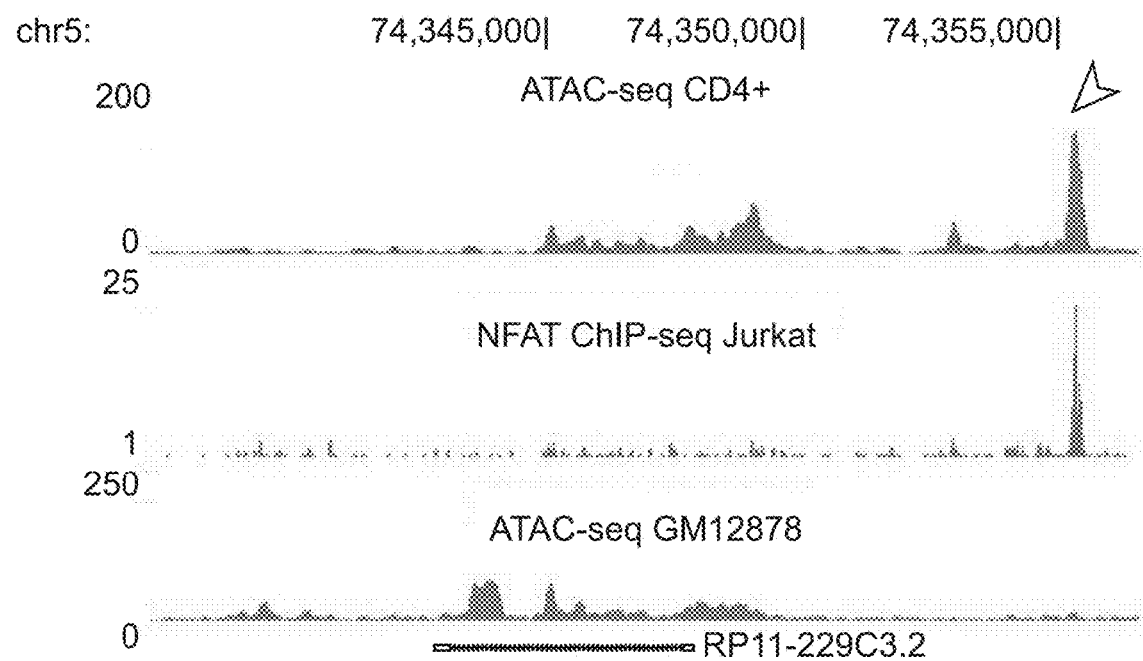
Figure 16:
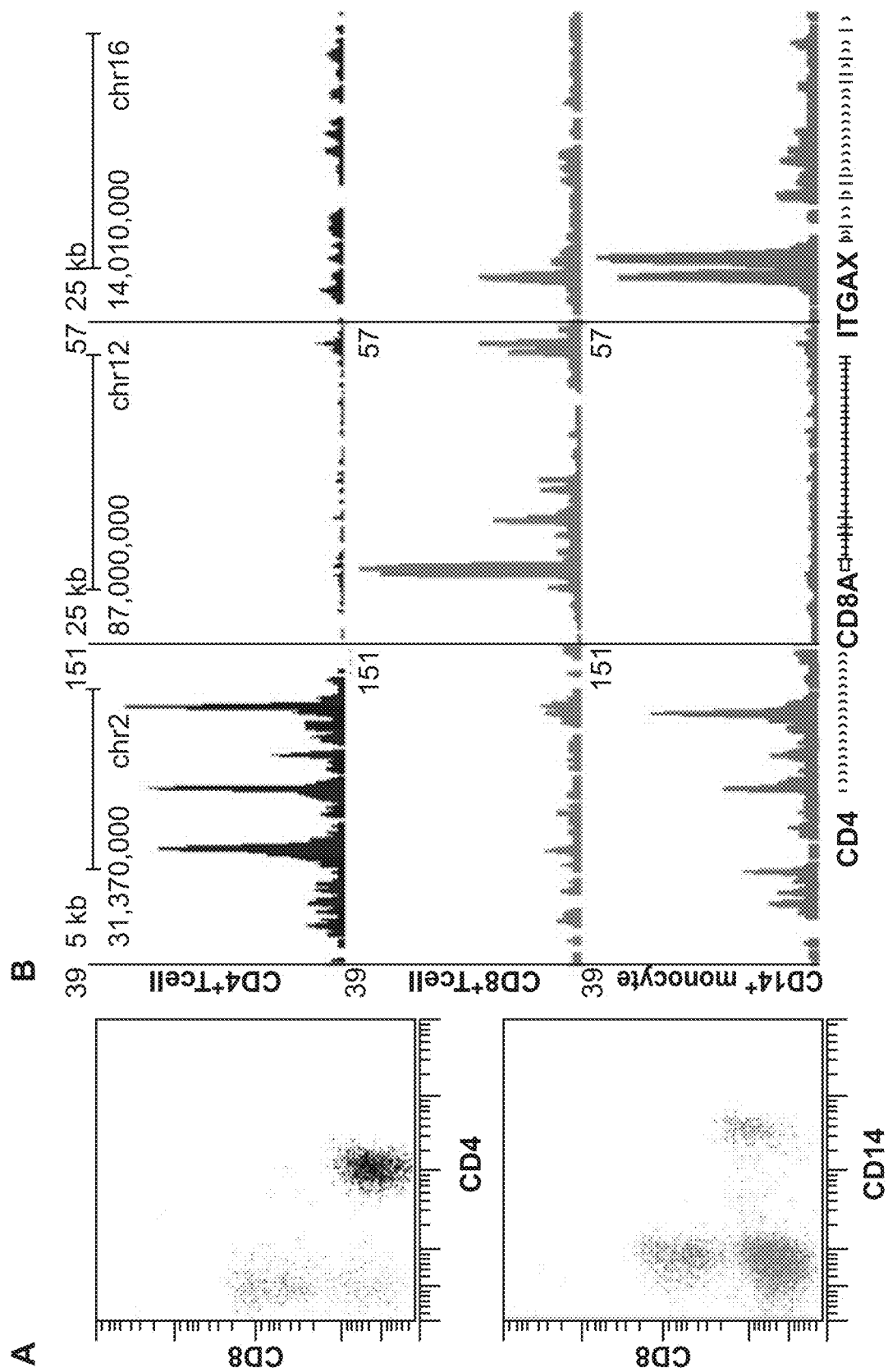
FIG. 16: ATAC-seq of FACS-purified cell populations from human blood. (A) From a standard blood draw, we used Fluorescence-Activated Cell Sorting (FACS) to purify CD4+ T-cells, CD8+ T-cells, and CD14+ monocytes. Each population generated successful ATAC-seq data (B) and revealed cell-type specific open chromatin sites at known lineage-specific genes.
Figure 17:
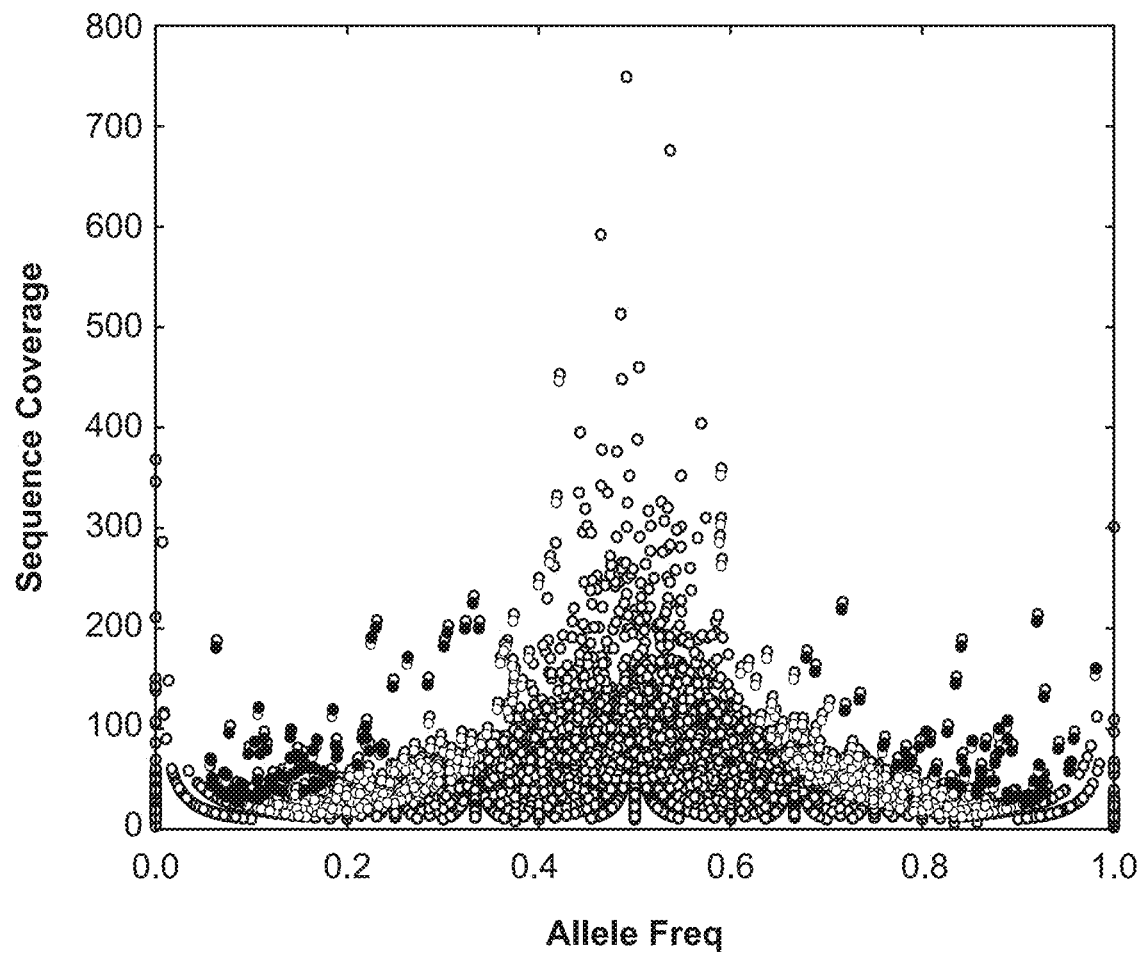
FIG. 17: Detection of allele specific open chromatin in GM12878 cells with ATAC-seq. Using publicly available variant data, we measured the allele frequency in open chromatin regions at putative heterozygous loci. Because of potential for spurious heterozygous sites, we required more than two reads to validate the heterozygosity of the allele. Red points (n=167) are candidate allele specific open chromatin sites at $p<10^{-5}$, while grey (n=900) represent candidates at p<0.01. P-values were calculated using a Bayesian model developed by Audic et al (Genome Research 1997 7, 986-995).

Using ATAC-seq footprints the occupancy profiles of 89 transcription factors in proband T-cells were generated, enabling systematic reconstruction of regulatory networks. With this personalized regulatory map, we compared the genomic distribution of the same 89 transcription factors between GM12878 and proband CD4+ T-cells. Transcription factors that exhibit large variation in distribution between T-cells and B-cells are enriched for T-cell specific factors (FIG. 5d). This analysis shows NFAT is differentially regulating, while canonical CTCF occupancy is highly correlated within these two cell types (FIG. 5d). Supporting this interpretation, it is noted that specific loci where NFAT is localized nearby to known T-cell specific genes such as CD28 and a novel lincRNA RP11-229C3.2 (FIG. 15). Additionally, ATAC-seq of $CD4^+$ and $CD8^+$ T-cells, and monocytes isolated by fluorescence-activated cell sorting (FACS) from a single blood draw created an interpretative framework for the personal epigenomes, and demonstrated that ATAC-seq is compatible with cellular enrichment using surface markers (FIG. 16). Separately, allele-specific chromatin accessibility has been shown to be particularly relevant to our understanding of human disease. As a proof of principle we also used ATAC-seq to identify candidate allele-specific open chromatin regions within the GM12878 cell line (FIG. 17). These results demonstrate the feasibility of generating detailed personalized gene regulatory networks from clinical samples, opening the door for future diagnostic applications.

Epigenomic studies of chromatin accessibility have yielded tremendous biological insights, but are currently limited in application by their complex workflows and large cell number requirements. While, improvements of existing methods may enable them to reach the similar performance, ATAC-seq in certain cases can offer substantial advantages over existing technologies due to its speed, simplicity, and low input cell number requirement. ATAC-seq is an information rich assay, allowing simultaneous interrogation of factor occupancy, nucleosome positions in regulatory sites, and chromatin accessibility genome-wide. These insights are derived from both the position of insertion and the distribution of insert lengths captured during the transposition reaction. While extant methods such as DNase- and MNase-seq can provide some subsets of the information in ATAC-seq, they each require separate assays with large cell numbers, which increases the time, cost, and limits applicability to many systems. ATAC-seq also provides insert size "fingerprints" of biologically relevant genomic regions, suggesting that it capture information on chromatin compaction. ATAC-seq may have broad applicability, significantly add to the genomics toolkit, and improve our understanding of gene regulation, particularly when integrated with other powerful rare cell techniques, such as FACS, laser capture microdissection (LCM) and recent advancements in RNA-seq.

ATAC-seq may be used to generate "personal epigenomic" profiles on a timescale compatible with clinical decision-making Optimized procedures can transform a clinical blood sample to completed sequencing library in 275 minutes. The reduced input requirements and rapid workflows, when coupled with the recent introduction of rapid-turnaround high-throughput sequencing instruments, such as the MiSeq and HiSeq2500, should enable investigation of personalized epigenetic landscapes of selected tissues both in the lab and the clinic. ATAC-seq is compatible with FACS, enabling studies on carefully sorted and rare subpopulations from primary tissues. Cellular subpopulations selected at different points in development and aging, and human diseases, including cancer, autoimmunity, and neuropsychiatric disorders are viable applications.

Example 2. Single-Cell ATAC-Seq

Single-cell chromatin accessibility datasets were obtained using the ATAC-seq protocol. To ensure that the ratio of transposase molecules to open chromatin sites was kept nearly constant, the single-cell ATAC-seq assay was carried out by manipulating individual cells after an initial transposition reaction.

Transposases can Serve as an Open-Chromatin Stain

Figure 18:
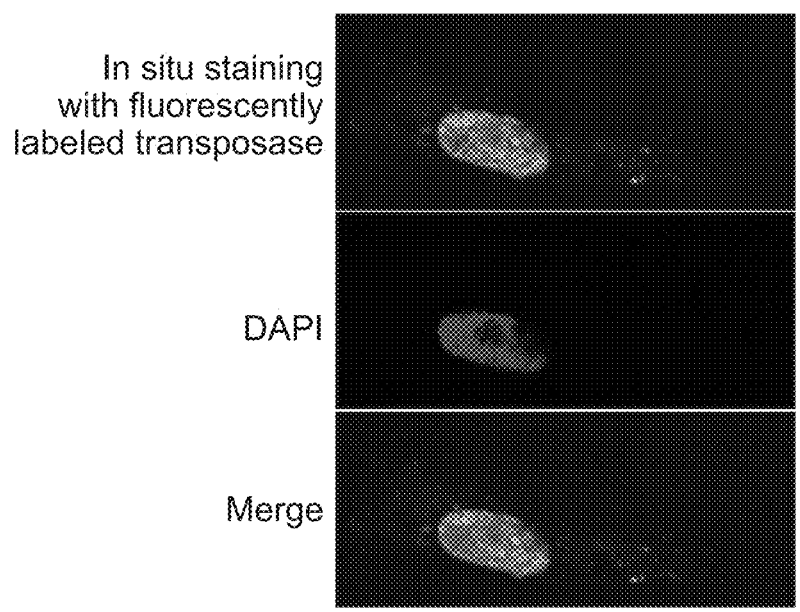
FIG. 18: Transposases can serve as an open-chromatin stain. By loading Tn5 transposes with fluorescently labeled DNA adapters, transposition events, shown in green, are primarily localized to the nucleus, and exhibit a punctate pattern consistent with higher order organization.

It was observed that after in vitro insertion of sequencing adapter, the Tn5 transposase remained tightly bound to the DNA and formed a high-affinity macromolecular complex that prevented dissociation of the generated ATAC-seq DNA fragments. To support this observation, Tn5 transposase was loaded with fluorescently labeled DNA adapters, and allowed for visualization of regions of open chromatin within the nucleus of individual cells (FIG. 18). Additional electrophoretic mobility shift assays also indicated that the transposase remained associated to DNA after transposition.

Single-Cell ATAC-Seq Provides Unique Reads Characteristic of Chromosomal DNA

Figure 19:
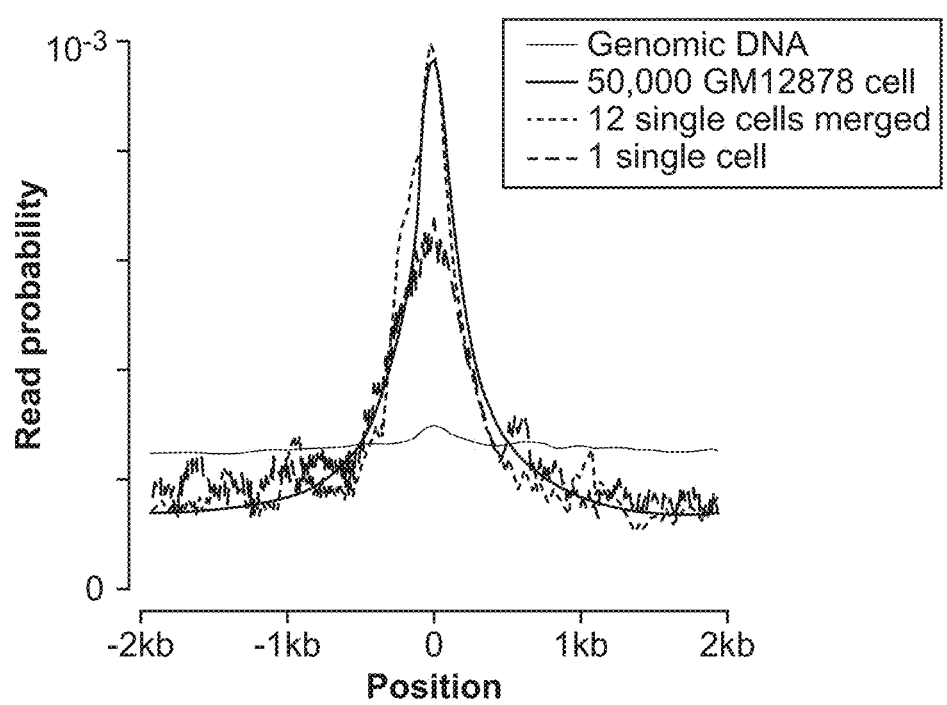
FIG. 19: Single-cell ATAC-seq data from a single nucleus (blue) show clear peak at the expected positions of open-chromatin genome wide compared to 50,000 cells.
Figure 20:
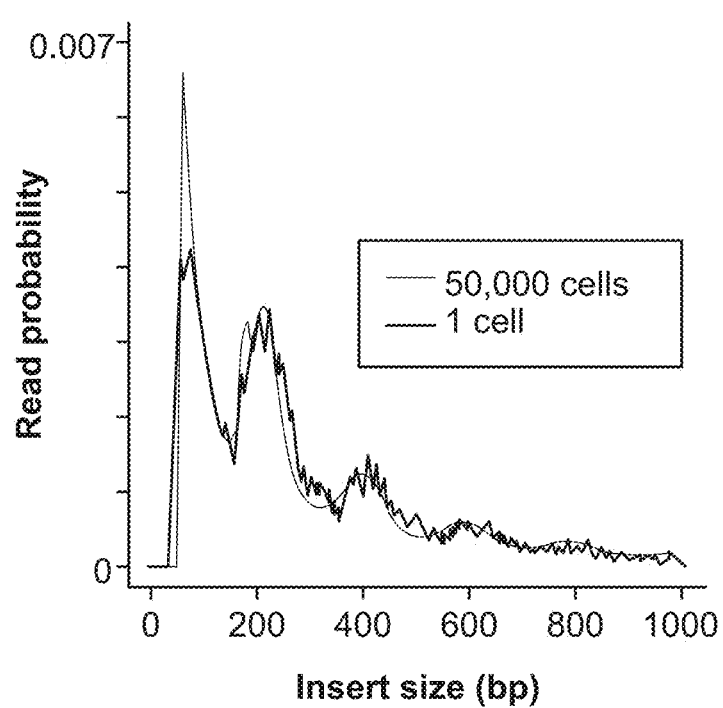
FIG. 20: Single cell insert length distribution matches that from 50,000 cells showing periodicity due to the presence of nucleosomes.

Since this fluorescence signal localized to the nucleus and was detectable even after transposition, the single-cell ATAC-seq experiment was performed by keeping the transposed fragments in the nucleus during subsequent sorting and cell selection steps. A group of cells were permeabilized, and the chromosomal DNA was transposed with Tn5 transposase. The cells were kept under conditions that prevented the resulting ATAC-seq fragments from leaving the cell nucleus, (i.e. divalent cation was not chelated), and the individual cells were sorted into independent PCR reactions for library preparation, as described above. This workflow significantly simplified the workflow for single-cell analysis and provided two additional advantages. First, this abrogated any effect of the sorting process on the chromatin state because transposition preceded sorting. Second, it provided more robust ATAC-seq signal, as cells were sorted directly into a PCR master mix and amplified. Using this workflow, ~2,000-5,000 unique ATAC-seq reads per cell were generated. These reads were enriched for known open chromatin sites in GM12878 cells (FIG. 19) and displayed characteristic periodic enrichments indicative of nucleosomes (FIG. 20).

Example 3. Quality Control

Assay for Transposase Accessible Chromatin (ATAC-seq) has been shown to be compatible with many methods for cell collection and has also worked effectively across many cell types and species. However, the following protocol has been optimized for human lymphoblastoid cells. Minor variations (i.e. cell number, centrifugation speeds, and lysis conditions) may optimized for particular applications.

I. Cell Preparation

1. Harvest cells (no fixation), protocol to be defined by the user.
2. Spin down 50,000 cells at 500×g for 5 mM, 4° C.
3. Wash once with 50 µL of cold 1×PBS buffer. Spin down at 500×g for 5 min, 4° C.
4. Gently pipette to resuspend the cell pellet in 50 µL of cold lysis buffer (10 mM Tris-HCl, pH 7.4, 10 mM NaCl, 3 mM $MgCl_2$, 0.1% IGEPAL CA-630). Spin down immediately at 500×g for 10 mM, 4° C.
5. Discard the supernatant, and immediately continue to transposition reaction.

II. Transposition Reaction and Purification

1. Make sure the cell pellet is set on ice.
2. To make the transposition reaction mix, combine the following:
   25 µL 2×TD Buffer (Illumina Cat #FC-121-1030)
   2.5 µL Tn5 Transposes (Illumina Cat #FC-121-1030)
   22.5 µL Nuclease Free $H_2O$
   50 µl Total
3. Gently pipette to resuspend nuclei in the transposition reaction mix.
4. Incubate the transposition reaction at 37° C. for 30 mM.
5. Immediately following transposition, purify using a Qiagen MinElute Kit.
6. Elute transposed DNA in 10 µL Elution Buffer (10 mM Tris buffer, pH 8).
7. Purified DNA can be stored at −20° C.

III. PCR Amplification

1. To amplify transposed DNA fragments, combine the following in a PCR tube:
   10 µL Transposed DNA
   9.7 µL Nuclease Free $H_2O$
   2.5 µL 25 µM Customized Nextera PCR Primer 1*
   2.5 µL 25 µM Customized Nextera PCR Primer 2* [Barcode]
   0.3 µL 100×SYBR Green I** (Invitrogen Cat #S-7563)
   25 µL NEBNext High-Fidelity 2×PCR Master Mix (New England Labs Cat #M0541)
   50 µL Total

* Complete list of primers are shown above.
   **10,000×SYBR Green I is diluted in 10 mM Tris buffer, pH 8 to make a 100× working solution.

2. Cycle as follows:
   (1) 72° C., 5 min
   (2) 98° C., 30 sec
   (3) 98° C., 10 sec
   (4) 63° C., 30 sec
   (5) 72° C., 1 min
   (6) Repeat steps 3-5, 4×
   (7) Hold at 4° C.
3. In order to reduce GC and size bias in PCR, the PCR reaction is monitored using qPCR to stop amplification prior to saturation. To run a qPCR side reaction, combine the following:
   5 µL 5 cycles PCR amplified DNA
   4.44 µL Nuclease Free $H_2O$
   0.25 µL 25 µM Customized Nextera PCR Primer 1*
   0.25 µL 25 µM Customized Nextera PCR Primer 2*
   0.06 µL 100×SYBR Green I
   5 µL NEBNext High-Fidelity 2×PCR Master Mix
   15 µL Total

* Complete list of primers available in Section VI of this protocol 4. qPCR cycle as follows:
   (1) 98° C., 30 sec
   (2) 98° C., 10 sec
   (3) 63° C., 30 sec
   (4) 72° C., 1 min
   (5) Repeat steps 2-4, 19×
   (6) Hold at 4° C.
5. The additional number of cycles needed for the remaining 45 µL PCR reaction is determined as following:
   (1) Plot linear Rn vs. Cycle
   (2) Set 5000 RF threshold
   (3) Calculate the # of cycle that is corresponded to ¼ of maximum fluorescent intensity
       If the # of cycle to be added lies in between two cycles, the # is determined by taking the smaller integer as the # of cycle to be added (i.e., blue and pink samples)
       If two samples have similar Ct values but differs in the fluorescent intensities, calculate the # of cycle using the sample with lower fluorescent intensity (i.e., red and blue samples)
6. Run the remaining 45 µL PCR reaction to the correct # of cycle. Cycle as follows:
   (1) 98° C., 30 sec (2) 98° C., 10 sec (3) 63° C., 30 sec (4) 72° C., 1 min (5) Repeat steps 2-4, × times (6) Hold at 4° C.
7. Purify amplified library using Qiagen PCR Cleanup Kit. Elute the purified library in 20 µL Elution Buffer (10 mM Tris Buffer, pH 8). Be sure to dry the column before adding elution buffer.

IV. Library QC Using Gel Electrophoresis

1. Dilute 1:20 100 bp NEB DNA ladder with 10 mM Tris Buffer, pH 8.
2. Add 0.6 µL 10×SYBR Green I to every 5 µL of diluted ladder.
3. Mix 1:1 of the diluted ladder with 2×DNA loading dye.
4. Mix 1:1 of amplified library with 2×DNA loading dye.
5. Run amplified library on 5% Bio-Rad Mini-Protean TBE Precast Gel (stored at 4° C.). Load 5 µL diluted ladder/DNA loading dye mixture. Load 10 µL amplified library/DNA loading dye mixture.
6. Run at ~100 mV for 45 min.
7. SYBR Green I dye has an excitation maximum at ~488 nm and has an emission maximum at ~520 nm. DNA stained with SYBR Green I dye can be visualized using a blue-light source or imaging systems equipped with laser that emits at 488 nm. We typically use Typhoon TRIO Variable Mode Imager from Amersham Biosciences for visualization. Images are best obtained by digitizing at 100 microns pixel size resolution with a 520 nm band-pass emission filter to screen out reflected and scattered excitation light and background fluorescence.

V. Library Quantitation

We use qPCR based methods to quantify our ATAC-seq libraries. We have found that other methods, such as Bioanalyzer and Qubit, can give misleading and inaccurate results due to the large distribution of insert sizes. We recommend quantifying libraries using the KAPA Library Quant Kit for Illumina Sequencing Platforms (KAPABiosystems).

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

What is claimed is:

1. A method for analyzing chromatin, comprising:
    (a) contacting chromatin in a permeabilized cell nucleus of a mammalian cell with an insertional enzyme complex such that polynucleotides of said permeabilized cell nucleus are cleaved and tagged at regions of open chromatin to produce a plurality of tagged nucleic acid fragments,
        wherein a tagged nucleic acid fragment comprises molecular tags comprising sequencing adaptors;
    (b) performing one or more nucleic acid reactions on the tagged nucleic acid fragments to produce a plurality of sequence reads; and
    (c) making an epigenetic map of a region of the permeabilized cell nucleus genome by mapping information obtained from the sequence reads to the region of the genome.

2. The method of claim 1, wherein the insertional enzyme complex comprises two different sequencing adaptors.

3. The method of claim 1, wherein a sequencing adaptor comprises a barcode label.

4. The method of claim 2, wherein a sequencing adaptor comprises a barcode label.

5. The method of claim 1, wherein the insertional enzyme complex comprises a hyperactive Tn5 transposase.

6. The method of claim 2, wherein the insertional enzyme complex comprises a hyperactive Tn5 transposase.

7. The method of claim 3, wherein the insertional enzyme complex comprises a hyperactive Tn5 transposase.

8. The method of claim 4, wherein the insertional enzyme complex comprises a hyperactive Tn5 transposase.

9. The method of claim 1, further comprising a step (a-1) of adding a barcode label to a sequencing adaptor after step (a), carried out under conditions that prevent the tagged nucleic acids fragments from leaving the permeabilized cell nucleus.

10. The method of claim 9, wherein the insertional enzyme complex comprises two different sequencing adaptors.

11. The method of claim 9, wherein the insertional enzyme complex comprises a hyperactive Tn5 transposase.

12. The method of claim 1, wherein the method is for analysis of chromatin of a single cell and further comprises a single cell sorting step (a-2) performed before step (b), and wherein step (a-2) is carried out under conditions that prevent the tagged nucleic acids fragments from leaving the permeabilized cell nucleus.

13. The method of claim 12, wherein the insertional enzyme complex comprises a hyperactive Tn5 transposase.

14. The method of claim 13, wherein the insertional enzyme complex comprises two different sequencing adaptors.

15. The method of claim 14, wherein a sequencing adaptor comprises a barcode label.

16. A method for analyzing chromatin, comprising:
(a) contacting chromatin in a permeabilized cell nucleus of a mammalian cell with an insertional enzyme complex such that polynucleotides of said permeabilized cell nucleus are cleaved and tagged at regions of open chromatin to produce a plurality of tagged nucleic acid fragments, wherein said insertional enzyme complex does not comprise an antibody specific to a protein that is part of said chromatin, and wherein a tagged nucleic acid fragment comprises molecular tags comprising sequencing adaptors;
(b) performing one or more nucleic acid reactions on the tagged nucleic acid fragments to produce a plurality of sequence reads; and
(c) making an epigenetic map of a region of the permeabilized cell nucleus genome by mapping information obtained from the sequence reads to the region of the genome.

17. The method of claim 16, wherein the insertional enzyme complex comprises two different sequencing adaptors.

18. The method of claim 16, wherein a sequencing adaptor comprises a barcode label.

19. The method of claim 17, wherein a sequencing adaptor comprises a barcode label.

20. The method of claim 16, wherein the insertional enzyme complex comprises a hyperactive Tn5 transposase.

21. The method of claim 17, wherein the insertional enzyme complex comprises a hyperactive Tn5 transposase.

22. The method of claim 18, wherein the insertional enzyme complex comprises a hyperactive Tn5 transposase.

23. The method of claim 19, wherein the insertional enzyme complex comprises a hyperactive Tn5 transposase.

24. The method of claim 16, further comprising a step (a-1) of adding a barcode label to a sequencing adaptor after step (a), carried out under conditions that prevent the tagged nucleic acids fragments from leaving the permeabilized cell nucleus.

25. The method of claim 24, wherein the insertional enzyme complex comprises two different sequencing adaptors.

26. The method of claim 24, wherein the insertional enzyme complex comprises a hyperactive Tn5 transposase.

27. The method of claim 16, wherein the method is for analysis of chromatin of a single cell and further comprises a single cell sorting step (a-2) performed before step (b), and wherein step (a-2) is carried out under conditions that prevent the tagged nucleic acids fragments from leaving the permeabilized cell nucleus.

28. The method of claim 27, wherein the insertional enzyme complex comprises a hyperactive Tn5 transposase.

29. The method of claim 28, wherein the insertional enzyme complex comprises two different sequencing adaptors.

30. The method of claim 29, wherein a sequencing adaptor comprises comprise a barcode label.

* * * * *